(12) United States Patent
Levine et al.

(10) Patent No.: US 9,480,464 B2
(45) Date of Patent: Nov. 1, 2016

(54) TISSUE COLLECTION SYSTEM

(75) Inventors: Jamie P. Levine, Scarsdale, NY (US);
Alexes Hazen, Brooklyn, NY (US);
Marc-Alan Levine, Pottstown, PA (US)

(73) Assignee: New York University, New York, NY (US)

( * ) Notice: Subject to any disclaimer, the term of this patent is extended or adjusted under 35 U.S.C. 154(b) by 920 days.

(21) Appl. No.: 13/561,722

(22) Filed: Jul. 30, 2012

(65) Prior Publication Data
US 2013/0030322 A1 Jan. 31, 2013

Related U.S. Application Data

(60) Provisional application No. 61/513,060, filed on Jul. 29, 2011.

(51) Int. Cl.
*A61B 10/02* (2006.01)

(52) U.S. Cl.
CPC .................. *A61B 10/0283* (2013.01)

(58) Field of Classification Search
CPC .............. A61B 10/02; A61B 10/0233; A61B 10/0283; A61B 2010/045; A61M 1/00; A61M 5/32
See application file for complete search history.

(56) References Cited

U.S. PATENT DOCUMENTS

| | | |
|---|---|---|
| 4,572,210 A | 2/1986 | McKinnon |
| 4,685,472 A | 8/1987 | Muto |
| 4,753,634 A | 6/1988 | Johnson |
| 4,834,703 A | 5/1989 | Dubrul et al. |
| 4,957,637 A | 9/1990 | Cornell |
| 5,019,045 A * | 5/1991 | Lee ............................... 604/110 |
| 5,024,660 A | 6/1991 | McNaughton |
| 5,030,209 A | 7/1991 | Wanderer et al. |
| 5,066,281 A | 11/1991 | Stevenson-Michener |
| 5,088,986 A | 2/1992 | Nusbaum |
| 5,156,599 A | 10/1992 | Ranford et al. |
| 5,259,841 A | 11/1993 | Hohendorf et al. |
| 5,300,038 A | 4/1994 | Haber et al. |
| 5,300,040 A | 4/1994 | Martin |
| 5,405,326 A | 4/1995 | Haber et al. |

(Continued)

FOREIGN PATENT DOCUMENTS

WO 89/09073 A1 10/1989

OTHER PUBLICATIONS

Shippert, "Autologous Fat Transfer: Eliminating Centrifuge, Decreasing Lipocyte Trauma and Establishing Standardization for Scientific Study," Am. J. Cosmetic Surgery 23(1):21-27 (2006).

(Continued)

*Primary Examiner* — Adam J Eiseman
*Assistant Examiner* — Yasmeen S Warsi
(74) *Attorney, Agent, or Firm* — LeClairRyan, a Professional Corporation

(57) ABSTRACT

The present invention relates to a tissue collection system. The system includes an outer housing, a first cylindrical fenestrated member within and immovable relative to the outer housing, a second cylindrical fenestrated member defining an inner tissue collection chamber and being positioned within and rotatable relative to the first cylindrical fenestrated member, a plunger axially movable within the second fenestrated member, an elongate rod being connected to the plunger, and one or more stop units attached to the outer housing. The present invention also relates to methods for separating components of a tissue sample using a system according to the present invention.

50 Claims, 23 Drawing Sheets

(56) References Cited

U.S. PATENT DOCUMENTS

| | | | |
|---|---|---|---|
| 5,485,853 | A | 1/1996 | Stubbs |
| 5,591,138 | A | 1/1997 | Vaillancourt |
| 5,807,344 | A | 9/1998 | Iwasaki |
| 6,287,282 | B1 | 9/2001 | Bonaldo et al. |
| 6,468,225 | B1 | 10/2002 | Lundgren |
| 6,471,677 | B2 | 10/2002 | Domici, Jr. |
| 6,527,742 | B1 | 3/2003 | Malenchek |
| 7,276,049 | B2 | 10/2007 | Bang et al. |
| 7,588,732 | B2 | 9/2009 | Buss |
| 7,704,237 | B2 * | 4/2010 | Fisher et al. ............. 604/208 |
| 8,202,493 | B2 | 6/2012 | Buss |
| 2003/0144630 | A1 | 7/2003 | Chang et al. |
| 2004/0153036 | A1 | 8/2004 | Fan |
| 2005/0054995 | A1 | 3/2005 | Barzell et al. |
| 2006/0182663 | A1 | 8/2006 | Uji et al. |
| 2006/0213374 | A1 * | 9/2006 | Shippert ............. 99/472 |
| 2007/0100277 | A1 | 5/2007 | Shippert |
| 2008/0091147 | A1 | 4/2008 | Lee |
| 2008/0154240 | A1 | 6/2008 | Shippert |
| 2008/0243028 | A1 | 10/2008 | Howard et al. |
| 2009/0287190 | A1 | 11/2009 | Shippert |
| 2011/0213336 | A1 | 9/2011 | Cucin |

OTHER PUBLICATIONS

"Shipped Tissu-Trans Syringe Fill 360cc Canister," Product Description, Mountainside Medical Equipment Company, http://www.mountainside-medical.com/products/Tiss%252dTrans-Syringe-FILL-360cc-Canister.html, 3 pages (accessed Jul. 16, 2012).

* cited by examiner

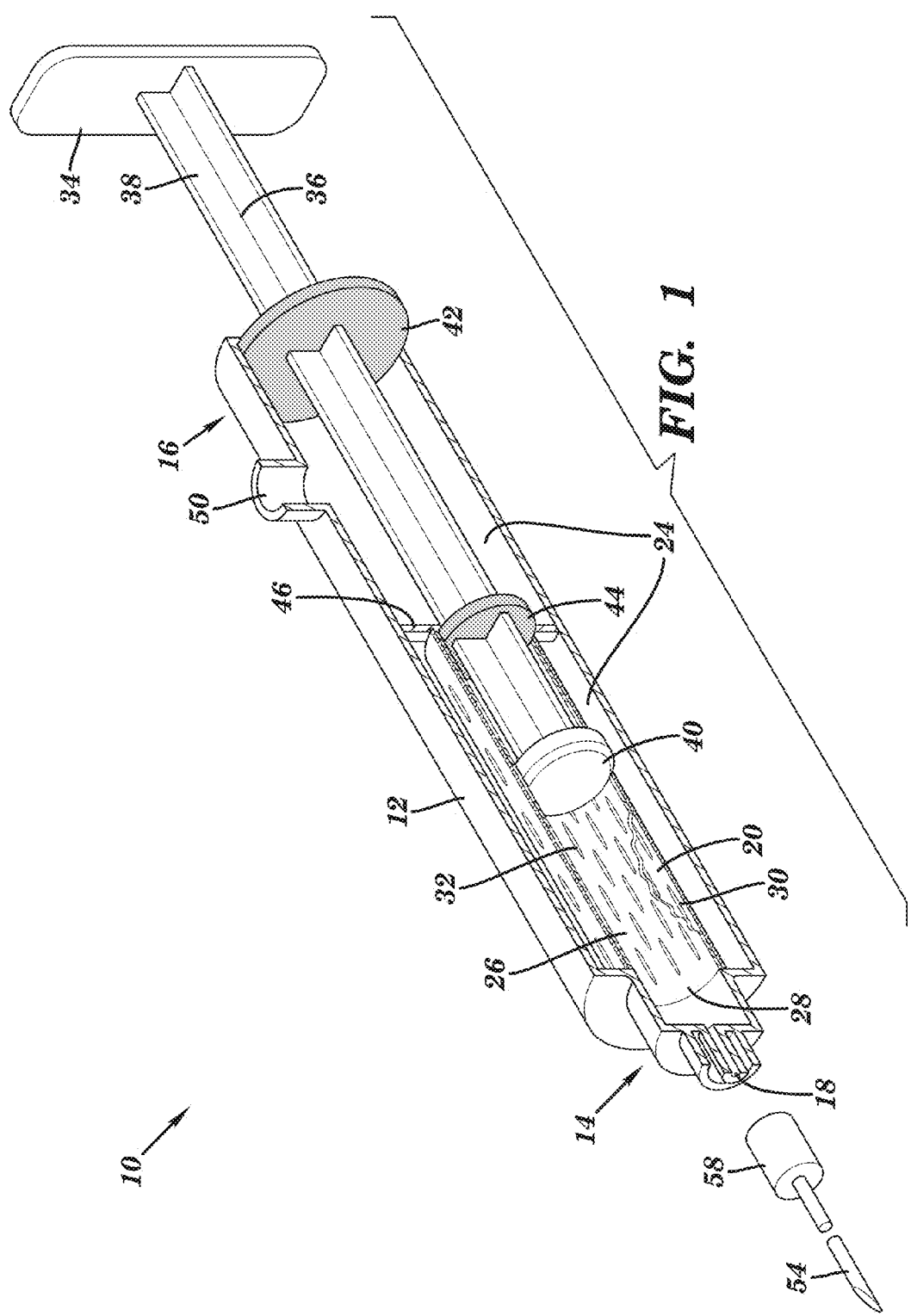

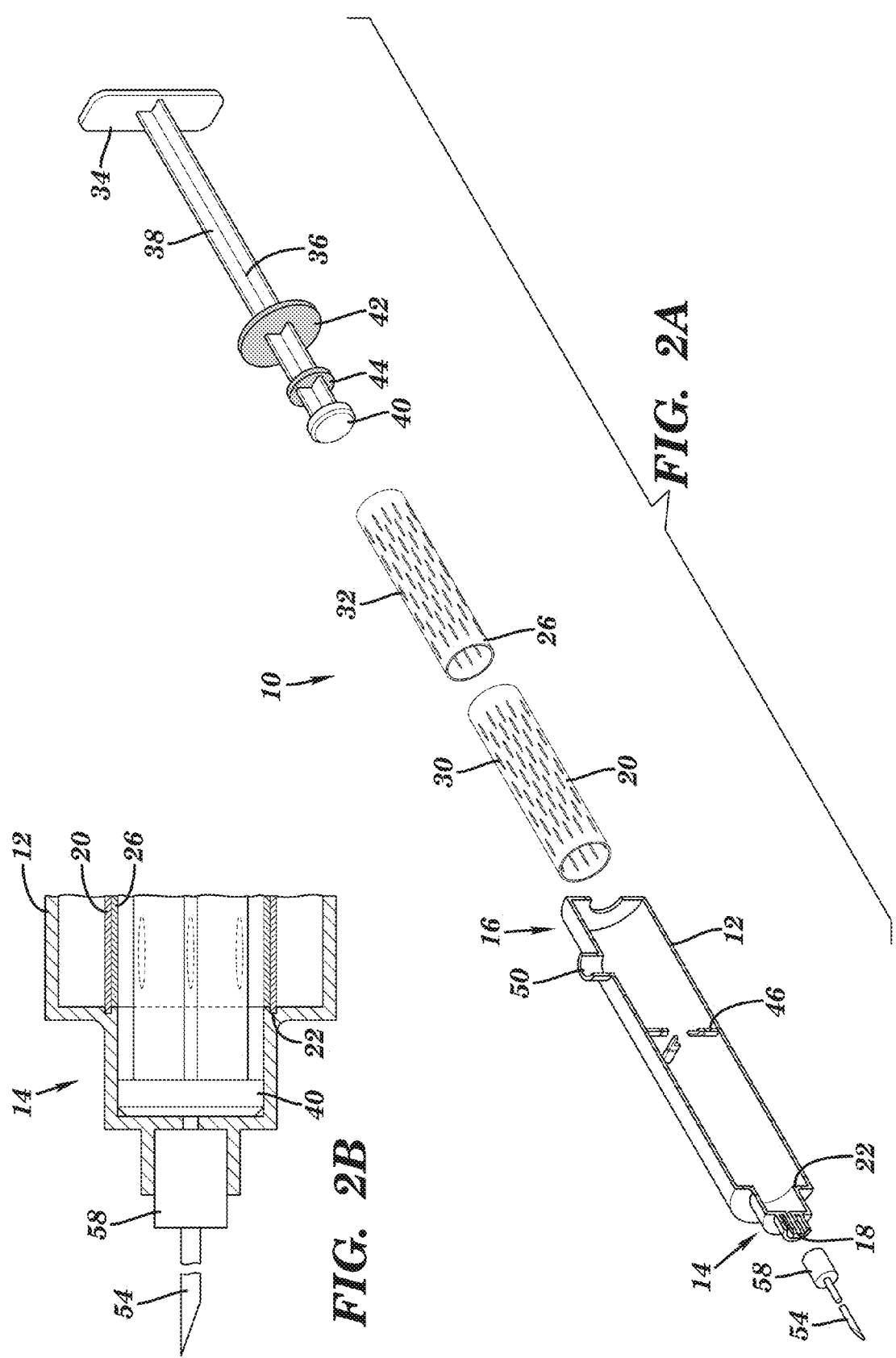

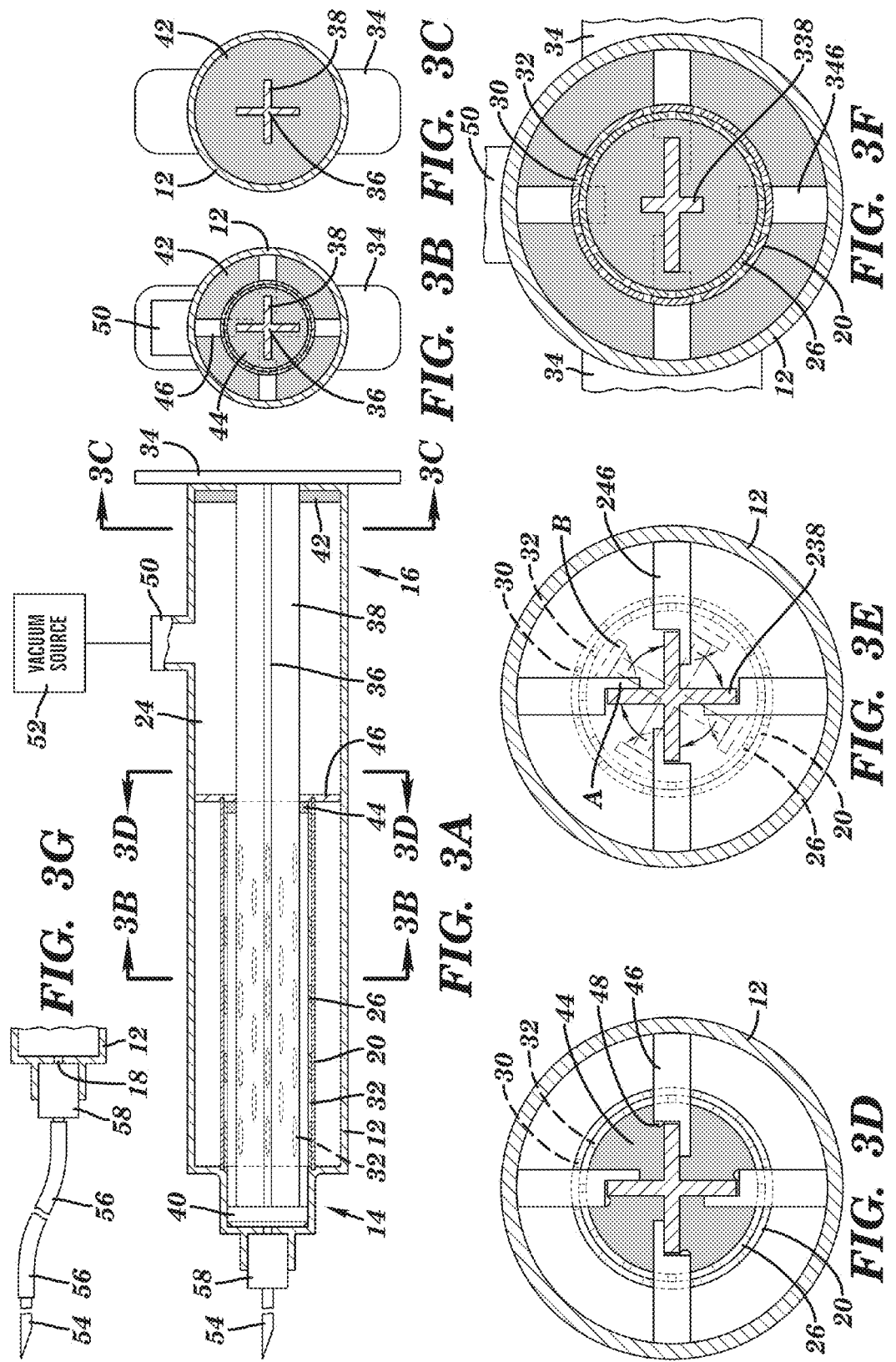

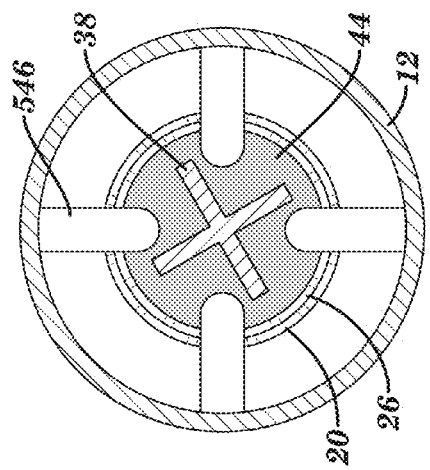
FIG. 4A
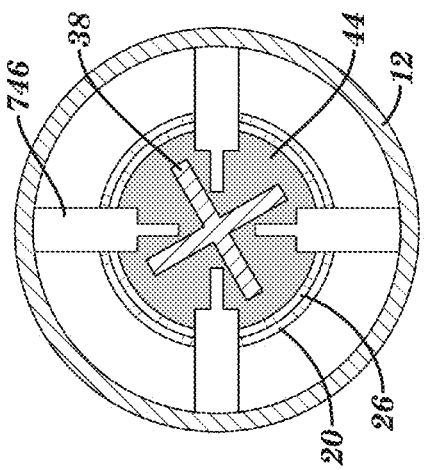
FIG. 4B
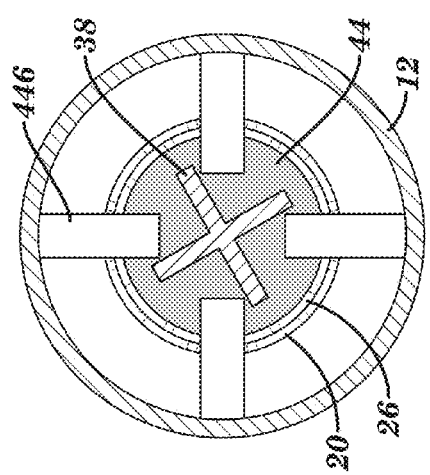
FIG. 4C
FIG. 4D

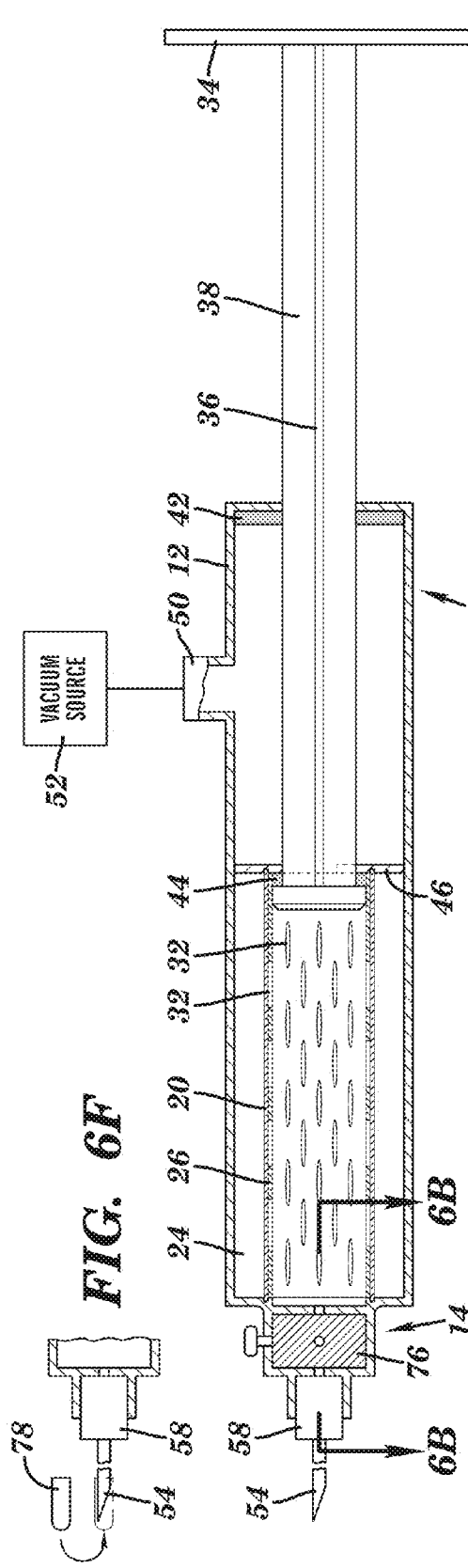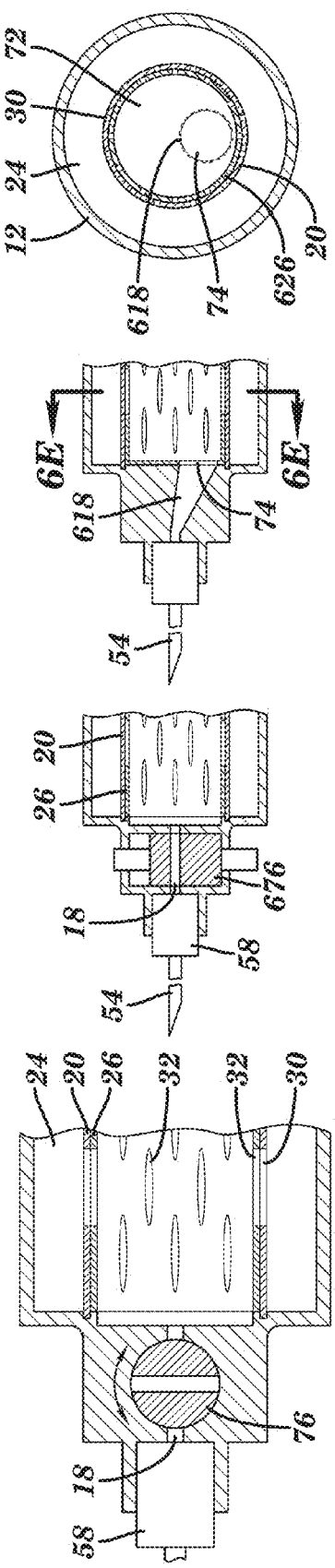

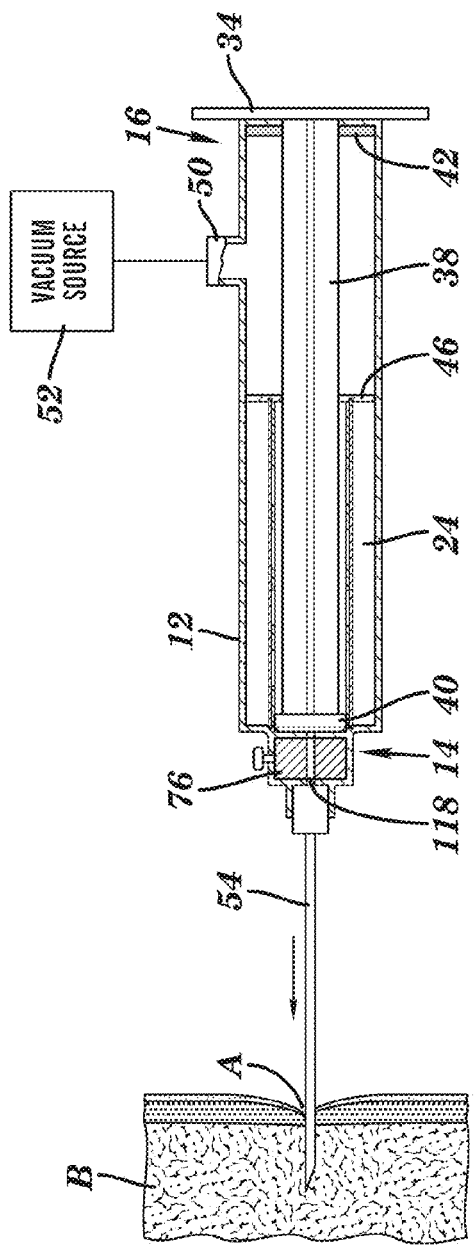
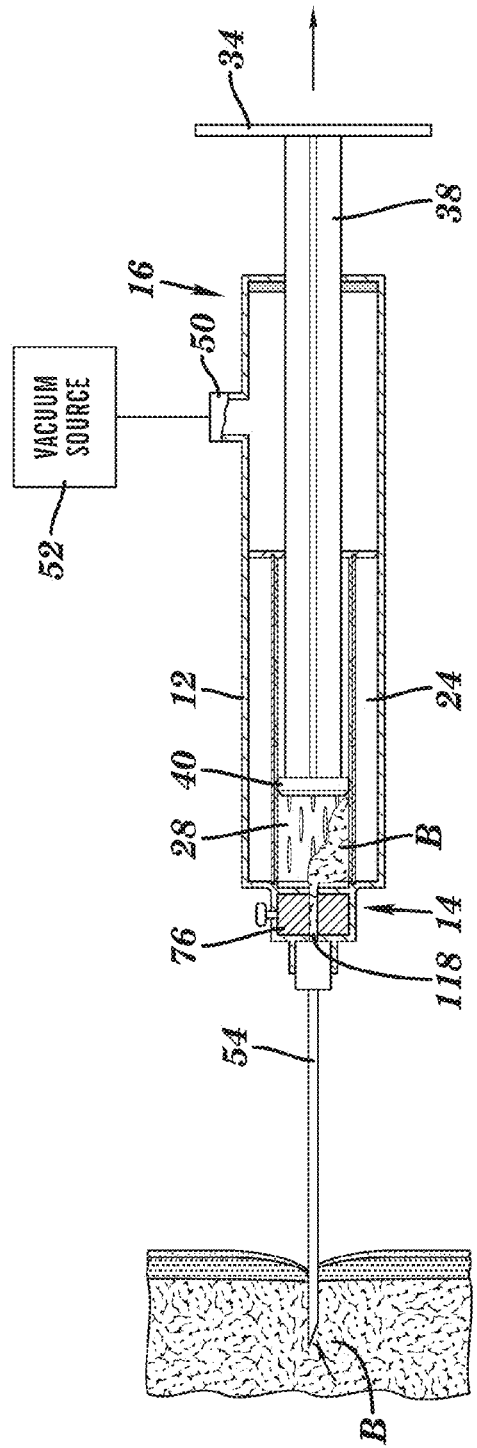
FIG. 8A
FIG. 8B

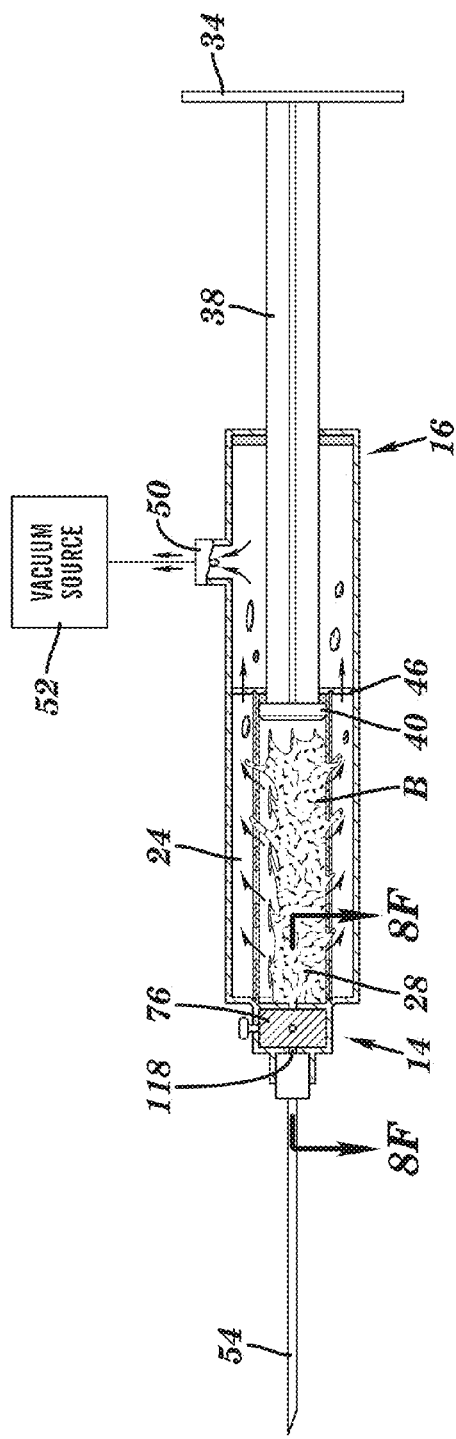
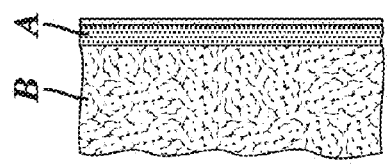
FIG. 8E
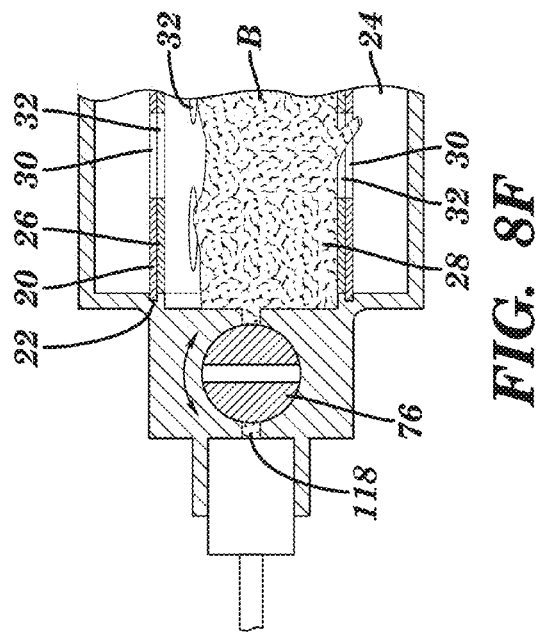
FIG. 8F

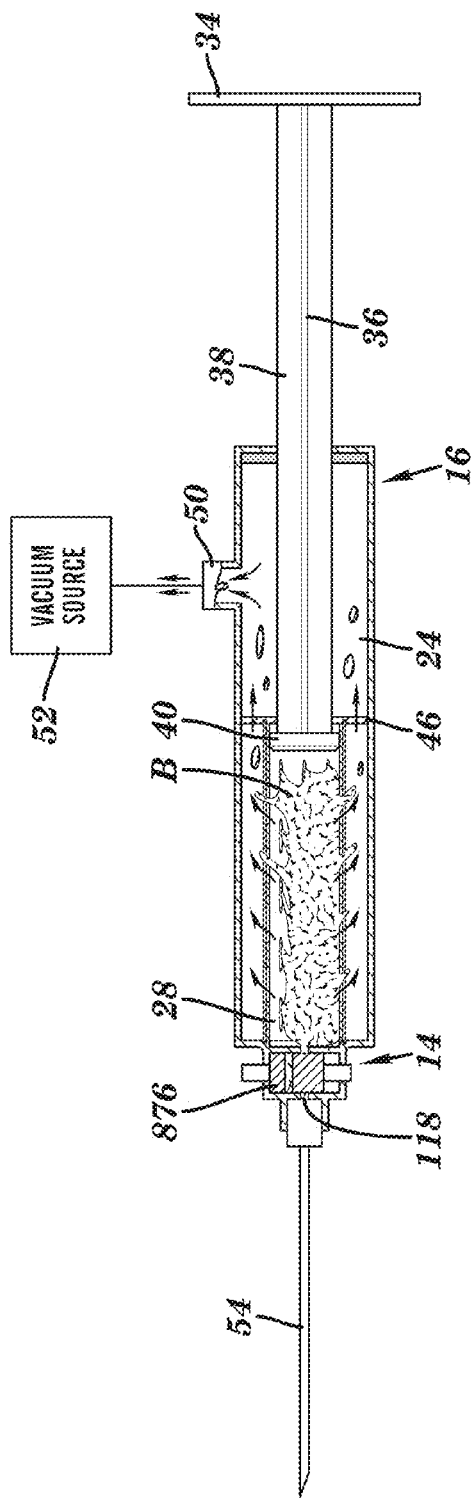
FIG. 8G
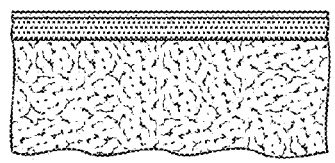

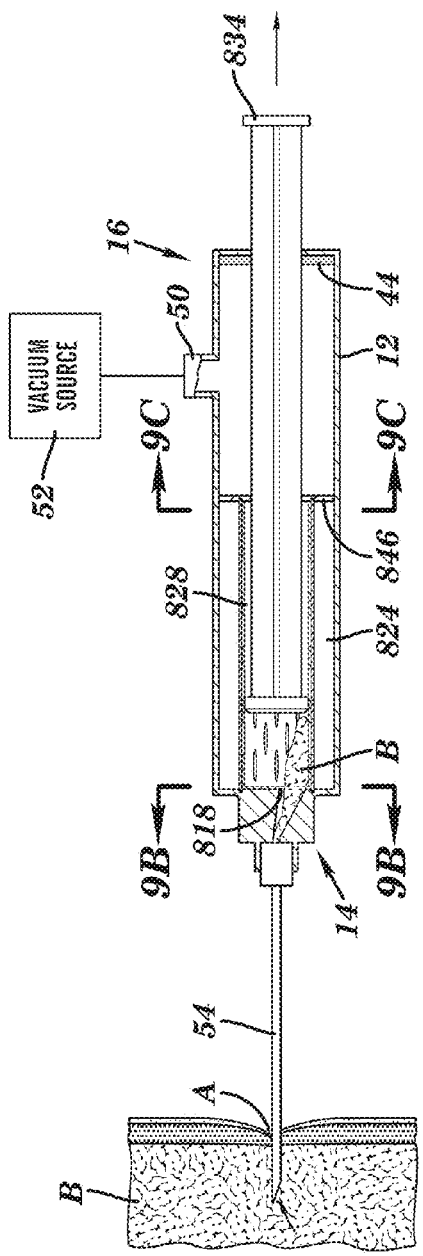
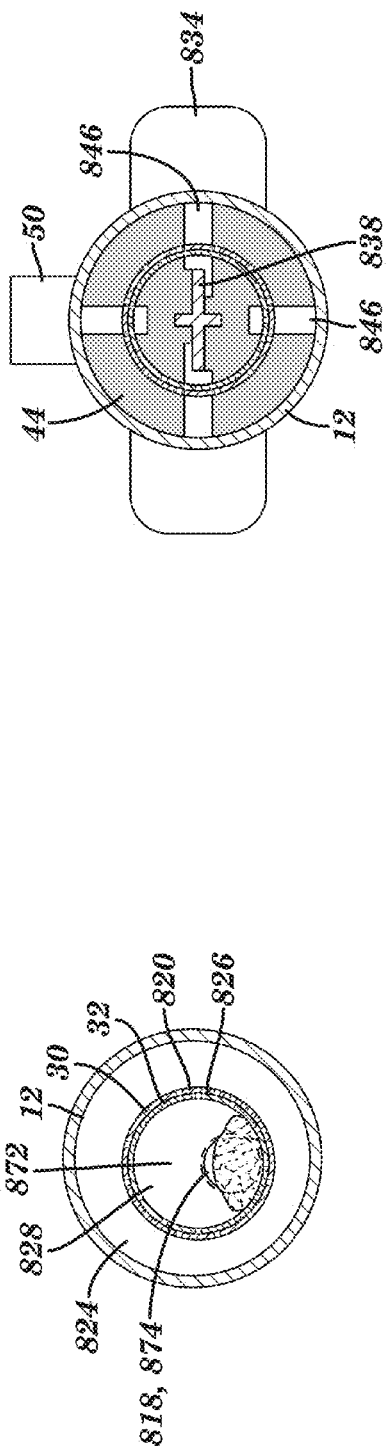
FIG. 9A
FIG. 9B
FIG. 9C

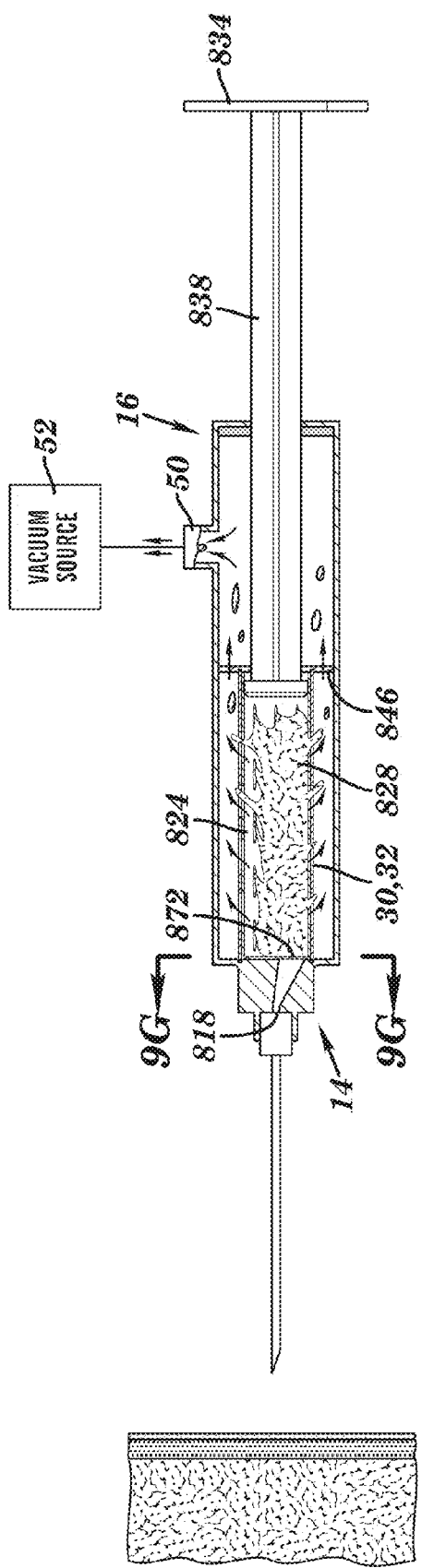
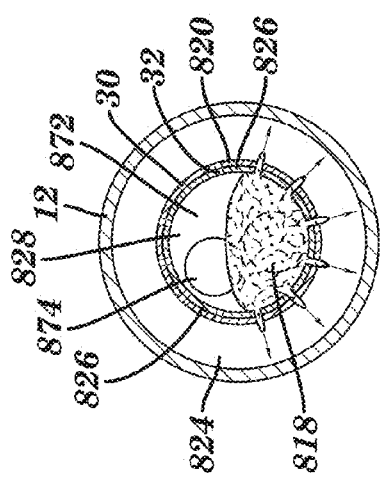
FIG. 9F
FIG. 9G

US 9,480,464 B2

TISSUE COLLECTION SYSTEM

This application claims benefit of U.S. Provisional Patent Application Ser. No. 61/513,060, filed Jul. 29, 2011, which is hereby incorporated by reference in its entirety.

FIELD OF THE INVENTION

This invention relates to a tissue collection system and methods of its use.

BACKGROUND OF THE INVENTION

The washing, treatment, and/or separation of tissue, for example to remove broken fat cell walls and contents, to remove chemicals introduced during the tissue removal process, to treat the removed tissue, or to separate excess fluid from removed tissue is often desirable. However, the washing, treatment, and/or refinement of tissue removed from a subject is particularly problematic, because conventional techniques for treating or washing the tissue often result in traumatic events for the tissue cells and increase the chance of microbe contamination.

In particular, conventional washing techniques have been time-consuming and expose the tissue to the hands of the surgical staff, exposes the tissue to the ambient air, and passes the tissue through different devices. This is because of the techniques involved: removing the tissue from the body; placing the removed tissue into a wash container; manually mixing sterile solution with the tissue; stirring the mixture; filtering it; centrifuging it; and then transferring it to the appropriate syringe for reinjection.

Accordingly, it would be desirable to reduce the time required to rid the specimen of unwanted, broken fat cell walls, broken fat cell contents, any other unnecessary extracellular fluid, as well as chemicals that have been introduced for anesthesia and vasoconstriction and/or to otherwise treat the removed tissue. In addition, it would be desirable to reduce the trauma to cells of removed tissue, and to reduce the chance of contamination of such tissue. Thus, there remains a great need for a streamline system for tissue harvest, refinement, preparation, and delivery.

Fat transfer is a procedure that is used to treat multiple disorders including post-traumatic injuries, congenital defects, and aesthetic problems. Fat transfer allows the affected soft tissue defect to be filled with autologous lipo-aspirate and offers the possibility of permanently repairing the affected area. One main reason for less widespread use of these techniques is that the entire process is cumbersome and requires multiple steps. These steps include harvesting, processing, and reinjection of the lipo-aspirate. These steps require multiple disposable and non-disposable tools. Each step also requires removal of the fat from the original collection container to another area for concentrating the fat and then placement of the fat, by hand, back into multiple syringes for injection. These multiple steps lengthen the procedure time and, because its switched from various syringes and collection devices, the fat has greater risk to be contaminated. If these processes can be simplified to utilize a single device for harvesting, processing, and reinjecting the lipo-aspirate, use of this technique can become more widespread.

The present invention overcomes these and other deficiencies in the art.

SUMMARY OF THE INVENTION

One aspect of the present invention relates to a tissue collection system. The tissue collection system comprises an outer housing having opposed distal and proximal ends, where the distal end is provided with an inlet passage. A first cylindrical fenestrated member is within and immovable relative to the outer housing, where an outer tissue collection chamber is defined between the outer housing and the first cylindrical fenestrated chamber. A second cylindrical fenestrated member defines an inner tissue collection chamber. The second cylindrical fenestrated member is positioned within and rotatable relative to the first cylindrical fenestrated member between an open position in which the fenestrations of the first cylindrical fenestrated member and the fenestrations of the second cylindrical fenestrated member are in registration with one another, thereby permitting fluid communication between the inner tissue collection chamber and the outer tissue collection chamber, and a closed position in which the fenestrations of the first cylindrical fenestrated member and the fenestrations of the second cylindrical fenestrated member are not in registration with one another, thereby preventing fluid communication between the inner tissue collection chamber and the outer tissue collection chamber. The system also comprises a plunger axially movable within the second fenestrated cylindrical member between an advanced position near the distal end of the outer housing and a retracted position near the proximal end of the outer housing. The plunger is rotatable to move the second cylindrical fenestrated member between the open and closed positions. The system further comprises an elongate rod being connected to the plunger to move the plunger axially between the advanced and retracted positions, and extending through the proximal end of the outer housing. One or more stop units are attached to the outer housing, extend into the outer tissue collection chamber, and are positioned to engage the elongate rod. This permits rotation of the rod and the plunger but restricts rotation of the second cylindrical fenestrated member between the open and closed positions.

Another aspect of the present invention relates to a method for separating components of a tissue sample. The method includes providing a system comprising an outer housing having opposed distal and proximal ends, where the distal end is provided with an inlet passage. A first cylindrical fenestrated member is within and immovable relative to the outer housing, where an outer tissue collection chamber is defined between the outer housing and the first cylindrical fenestrated chamber. A second cylindrical fenestrated member defines an inner tissue collection chamber and is positioned within and rotatable relative to the first cylindrical fenestrated member between an open position and a closed position. In the open position, the fenestrations of the first cylindrical fenestrated member and the fenestrations of the second cylindrical fenestrated member are in registration with one another, thereby permitting fluid communication between the inner tissue collection chamber and the outer tissue collection chamber. In the closed position, the fenestrations of the first cylindrical fenestrated member and the fenestrations of the second cylindrical fenestrated member are not in registration with one another, thereby preventing fluid communication between the inner tissue collection chamber and the outer tissue collection chamber. A plunger is axially movable within the second fenestrated cylindrical member between an advanced position near the distal end of the outer housing and a retracted position near the proximal end of the outer housing. The plunger is rotatable to move the second cylindrical fenestrated member between the open and closed positions. An elongate rod having a plurality of longitudinally-extending ribs is connected to the plunger to move the plunger axially between the advanced and retracted positions, and extends through the proximal end of the outer housing. One or more stop units are attached to the outer housing, extending into the outer tissue collection chamber, and positioned to engage the ribs, permitting rotation of the rod and the plunger but restricting rotation of the second cylindrical fenestrated member between the open and closed positions. The method also includes placing the inlet in contact with the fluid sample with the plunger in the advanced position and the first and second cylindrical fenestrated members in the closed position. The plunger is then moved with the rod to the retracted position to draw the fluid sample into the inner tissue collection chamber.

The systems and methods according to the present invention provide a streamline system for tissue collection. One main reason for less widespread use of these techniques is that the entire process is cumbersome and requires multiple steps. These steps include harvesting, processing that often requires multiple devices, and then reinjection of the, e.g., lipo-aspirate. These steps require multiple disposable and non-disposable items. The processing portion requires removal from the syringe, some form of concentrating the fat (e.g., centrifuging) and replacement of the concentrated fat into syringes for injection. By simplifying the system to a single device for the harvesting, processing, and reinjection of the lipo-aspirate, the use of this technique can become more widespread and uniform. With the advent of a simpler and safer methodology of harvesting, processing, and transfer there is no doubt that use of these techniques will increase significantly. With the creation of a single, disposable device to easily perform all the functions of this cumbersome process, the training of professionals will be shortened. The systems and methods according to the present invention can easily allow for the augmentation of, e.g., fat tissue with any number of growth factors or stimulatory agents. In addition, systems and methods according to the present invention are easily used or adapted to harvest and/or process other types of tissue, fluids, semi solids, or solids.

All of the harvesting, processing, and delivery of, e.g., fat will be contained within the system according to the present invention. This requires less disposable and non-disposable equipment. Also, since the systems according to the present invention may be single use, with minimal or no transfer of the tissue between other syringes and collection basins, the safety is improved and the risks of contamination will be decreased. This is both because the device may be disposable and no processing in separate systems or devices is necessarily required.

BRIEF DESCRIPTION OF THE DRAWINGS

FIG. 1 is a partly cut away perspective view of one embodiment of a tissue collection system according to the present invention.

FIG. 2A is a partially cross-sectional exploded perspective view of one embodiment of a tissue collection system according to the present invention. FIG. 2B is a partially exploded cross-sectional view of FIG. 2A showing a cylindrical groove at the outer housing distal end.

FIGS. 3A to 3G are various cross-sectional views of a tissue collection system according to the present invention. FIG. 3A is a longitudinal cross-sectional view. FIG. 3B is a cross-sectional end view along line 3B-3B of FIG. 3A. FIG. 3C is a cross-sectional end view along line 3C-3C of FIG. 3A. FIG. 3D is a cross-sectional end view of a stop unit taken along line 3D-3D of FIG. 3A. FIGS. 3E and 3F show various other embodiments of stop units and ribs according to the present invention. FIG. 3G is a partial cross-sectional view of a cannula and conduit according to the present invention.

FIGS. 4A to 4D are end cross sectional views of a tissue collection system according to the present invention showing various embodiments of stop units according to the present invention.

FIGS. 5A to 5C are perspective views of cylindrical fenestrated members according to the present invention. FIGS. 5D and 5E are partial end cross-sectional views of individual fenestrations according to the present invention.

FIGS. 6A to 6F are cross-sectional views of various embodiments of an inlet sealing means according to the present invention. FIGS. 6A, 6C, and 6F are longitudinal cross-sectional views. FIG. 6B is a cross-sectional view along line 6B-6B of FIG. 6A. FIG. 6C is a partial cross-sectional view of an embodiment other than that shown in FIG. 6A, along the same plane and direction as that of line 6B-6B of FIG. 6A. FIG. 6D is a partial longitudinal cross-sectional view of an inlet according to the present invention. FIG. 6E is an end view along line 6E-6E of FIG. 6D.

FIG. 7A is a schematic longitudinal cross-sectional view illustrating a tissue collection system according to the present invention penetrating body tissue at a donor site. FIG. 7B is a schematic longitudinal cross-sectional view illustrating a tissue collection system according to the present invention aspirating or collecting body tissue from a donor site. FIG. 7C is a longitudinal cross-sectional view showing the tissue collection system withdrawn from the body and the rotation of the plunger and, in turn, the second fenestrated member to the open position. FIG. 7D is a schematic cross-sectional view along line 7D-7D of FIG. 7C illustrating the second cylindrical fenestrated member rotating from closed (A) to open (B) positions. FIG. 7E is a schematic longitudinal cross-sectional view of sealing the inlet by capping and applying a vacuum to the outlet while the one or more fenestrations of the system are aligned. FIG. 7F is a longitudinal cross-sectional view showing the tissue collection system prepared for reinjection of tissue into the body by the rotation of the plunger and, in turn, the second fenestrated member to the closed position. FIG. 7G is a schematic cross-sectional end view along line 7G-7G of FIG. 7F illustrating the second cylindrical fenestrated member rotating from open (B) to closed (A) positions. FIG. 7H is a longitudinal cross-sectional view of a tissue collection system according to the present invention reinjecting tissue into the body.

FIGS. 8A to 8J are a series of schematic cross-sectional views illustrating operation of a tissue collection system according to the present invention that includes a valve sealing means. FIG. 8A is a schematic longitudinal cross-sectional view illustrating a tissue collection system according to the present invention penetrating body tissue at a donor site. FIG. 8B is a schematic longitudinal cross-sectional view illustrating a tissue collection system according to the present invention aspirating or collecting body tissue from a donor site. FIG. 8C is a longitudinal cross-sectional view showing the tissue collection system withdrawn from the body and the rotation of the plunger and, in turn, the second fenestrated member to the open position. FIG. 8D is a schematic cross-sectional view along line 8D-8D of FIG. 8C illustrating the second cylindrical fenestrated member in rotating from closed (A) to open (B) positions. FIG. 8E is a schematic longitudinal cross-sectional view of sealing the inlet by operating a valve sealing means according to the present invention and applying a vacuum to the outlet while the one or more fenestrations of the system are aligned. FIG. 8F is a partial longitudinal cross-sectional view along line 8F-8F of FIG. 8E showing the operation of a valve sealing means according to the present invention. FIG. 8G is a schematic longitudinal cross-sectional view of sealing the inlet by operating an alternative valve sealing means according to the present invention and applying a vacuum to the outlet while the one or more fenestrations of the system are aligned. FIG. 8H is a longitudinal cross-sectional schematic view showing the tissue collection system preparing for reinjection of tissue into the body by the rotation of the plunger and, in turn, the second fenestrated member to the closed position. FIG. 8I is a schematic cross-sectional end view along line 8I-8I of FIG. 8H illustrating the second cylindrical fenestrated member rotating from open (B) to closed (A) positions. FIG. 8J is a longitudinal cross-sectional view of a tissue collection system according to the present invention reinjecting tissue into the body.

FIGS. 9A to 9J are a series of schematic cross-sectional views illustrating operation of a tissue collection system according to the present invention that includes an alternate inlet sealing means. FIG. 9A is a schematic longitudinal cross-sectional view illustrating a tissue collection system according to the present invention aspirating or collecting body tissue from a donor site. FIG. 9B is a schematic cross-sectional end view along line 9B-9B of FIG. 9A. FIG. 9C is a cross-sectional end view along line 9C-9C of FIG. 9A showing the second cylindrical fenestrated member in the closed position. FIG. 9D is a longitudinal cross-sectional view showing the tissue collection system withdrawn from the body and the rotation of the plunger and, in turn, the second fenestrated member to the open position. FIG. 9E is a schematic cross-sectional view along line 9E-9E of FIG. 9D illustrating the second cylindrical fenestrated member in rotating from closed (A) to open (B) positions. FIG. 9F is a schematic longitudinal cross-sectional view of sealing the inlet by operating an alternative inlet sealing means according to the present invention and applying a vacuum to the outlet while the one or more fenestrations of the system are aligned. FIG. 9G is a schematic cross-sectional end view along line 9G-9G of FIG. 9F showing the sealing of the inlet according to one embodiment of the present invention. FIG. 9H is a longitudinal cross-sectional schematic view showing the tissue collection system preparing for reinjection of tissue into the body by the rotation of the plunger and, in turn, the second fenestrated member to the closed position. FIG. 9I is a schematic cross-sectional end view along line 9I-9I of FIG. 9H illustrating the second cylindrical fenestrated member rotating from open (B) to closed (A) positions. FIG. 9J is a longitudinal cross-sectional view of a tissue collection system according to the present invention reinjecting tissue into the body.

DETAILED DESCRIPTION OF THE INVENTION

Figure 5A:
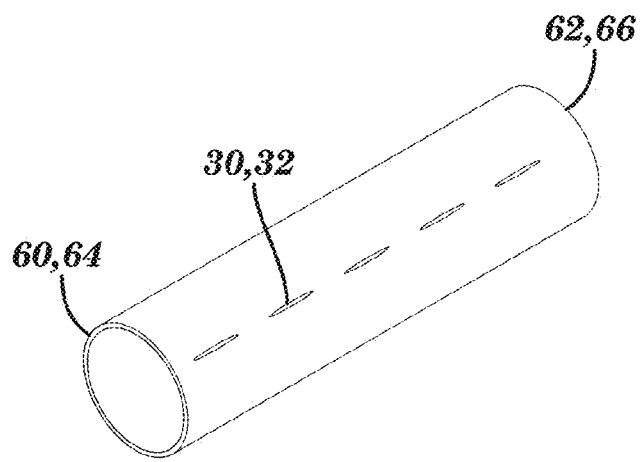
FIGS. 5A to 5E show various embodiments of cylindrical fenestrated members as well as fenestrations and filters according to the present invention.

The following detailed description refers to the accompanying drawings. Like reference numbers are used throughout to refer to like elements.

One aspect of the present invention relates to a tissue collection system. The tissue collection system comprises an outer housing having opposed distal and proximal ends, where the distal end is provided with an inlet passage. A first cylindrical fenestrated member is within and immovable relative to the outer housing, where an outer tissue collection chamber is defined between the outer housing and the first cylindrical fenestrated chamber. A second cylindrical fenestrated member defines an inner tissue collection chamber. The second cylindrical fenestrated member is positioned within and rotatable relative to the first cylindrical fenestrated member between an open position in which the fenestrations of the first cylindrical fenestrated member and the fenestrations of the second cylindrical fenestrated member are in registration with one another, thereby permitting fluid communication between the inner tissue collection chamber and the outer tissue collection chamber, and a closed position in which the fenestrations of the first cylindrical fenestrated member and the fenestrations of the second cylindrical fenestrated member are not in registration with one another, thereby preventing fluid communication between the inner tissue collection chamber and the outer tissue collection chamber. The system also comprises a plunger axially movable within the second fenestrated cylindrical member between an advanced position near the distal end of the outer housing and a retracted position near the proximal end of the outer housing. The plunger is rotatable to move the second cylindrical fenestrated member between the open and closed positions. The system further comprises an elongate rod being connected to the plunger to move the plunger axially between the advanced and retracted positions, and extending through the proximal end of the outer housing. One or more stop units are attached to the outer housing, extend into the outer tissue collection chamber, and are positioned to engage the elongate rod. This permits rotation of the rod and the plunger but restricts rotation of the second cylindrical fenestrated member between the open and closed positions.

Referring now to FIGS. 1 and 2A, tissue collection system 10 is shown in a cross-sectional view (FIG. 1) and a partially exploded cross-sectional view (FIG. 2A). Tissue or fluid collection system 10 includes outer housing 12 with opposed outer housing distal end 14 and outer housing proximal end 16. Outer housing 12 includes inlet passage 18 at or near outer housing distal end 14.

Tissue or fluid collection system 10 also includes first cylindrical fenestrated member 20 within outer housing 12. In certain embodiments, first cylindrical fenestrated member 20 is immovable or substantially immovable relative to outer housing 12. This may be accomplished by permanently or temporarily fixing first cylindrical fenestrated member 20 to outer housing 12, which may be accomplished by any means known to those of skill in the art (e.g., close fitting contact, press fit, glue, mechanical lock, cooperating threads, or other means that will be known to those of skill in the art). Alternatively, outer housing 12 and first cylindrical fenestrated member 20 may be molded or cast to form a single continuous piece or unit. In one embodiment, first cylindrical fenestrated member 20 is held in cylindrical groove 22 formed at outer housing distal end 14, as shown in FIG. 2B. First cylindrical fenestrated member 20 may be permanently or temporarily held in cylindrical groove 22 by, e.g., close fitting contact, press fit, glue, mechanical lock, cooperating threads, or other means that will be known to those of skill in the art. First cylindrical fenestrated member 20 may alternatively extend to inlet passage 18. In certain embodiments, first cylindrical fenestrated member 20 may be made immovable by being fixed temporarily or permanently to inlet passage 18. In this embodiment, a bore or inlet in first cylindrical fenestrated member 20 will correspond to the inner diameter of inlet passage 18 and, in certain embodiments, inlet passage 18 will receive first cylindrical fenestrated member 20. This can be achieved by interior diameter of inlet passage 18 receiving first cylindrical fenestrated member 20 and being held permanently or temporarily, as previously described.

With further reference to FIG. 1, outer tissue collection chamber 24 is defined between outer housing 12 and first cylindrical fenestrated member 20. Outer tissue collection chamber 24 has an interior volume that is sufficient to house first and second cylindrical fenestrated members 20, 26.

Second cylindrical fenestrated member 26 is positioned within first cylindrical fenestrated member 20 (shown in partial cut away of FIG. 1) and also rotatable relative to first cylindrical fenestrated member 20. Second cylindrical fenestrated member 26 also defines inner tissue collection chamber 28. Second cylindrical fenestrated member 26 is positioned within first cylindrical fenestrated member 20 such that a seal is maintained when one or more fenestrations 30, 32 of the respective first and second cylindrical fenestrated members 20, 26 are not registered or aligned. By seal it is meant that inner and outer tissue collection chambers 28, 24 are not in fluid communication with one another (i.e., inner tissue collection chamber 28 is substantially or completely sealed from outer tissue collection chamber 24). This may be achieved in a number of ways that will be known to those of skill in the art. For example, this may be achieved by close fitting contact between first and second cylindrical fenestrated members 20 and 26. Close-fitting contact between first and second cylindrical fenestrated members 20 and 26 may be achieved and maintained by first and second cylindrical fenestrated members 20 and 26 being held in cylindrical groove 22, as described above. This may also be accomplished by, e.g., an o-ring like silicon grommet that is attached at the outside bottom of first cylindrical fenestrated member 20 or second cylindrical fenestrated member 26 may be press fit to the inner diameter of first cylindrical fenestrated members 20.

As will be described in further detail below, second cylindrical fenestrated member 26 may be rotated between an open and a closed position. In the open position, one or more fenestrations 30 of first cylindrical fenestrated member 20 and one or more fenestrations 32 of second cylindrical fenestrated member 26 are in registration or aligned with one another. Upon substantial alignment or registration of one or more fenestrations 30 of first cylindrical fenestrated member 20 and one or more fenestrations 32 of second cylindrical fenestrated member 26, fluid communication between inner tissue collection chamber 28 and outer tissue collection chamber 24 is permitted. As will be understood by those of skill in the art, variable degrees of fluid communication will be permitted as second cylindrical fenestrated member 26 is rotated relative to first cylindrical fenestrated member 20.

With further reference to FIGS. 1, 2, and 3A tissue or fluid collection system 10 also includes plunger 34. Plunger 34 comprises an elongate rod 36. In one embodiment, elongate rod 36 comprises one or more longitudinally extending ribs 38. It will be understood that elongate rod 36 may include any number of ribs 38. In certain embodiments, elongate rod 36 comprises a plurality of longitudinally extending ribs 38. In one embodiment, elongate rod 36 includes 1, 2, 3, or 4 ribs. Ribs 38 may extend varying or the same radial distances relative to one another.

Elongate rod 36 may also include rod end 40. Rod end 40 is slidably and sealingly engaged with the interior diameter of second cylindrical fenestrated member 26 or, when plunger 34 is in the advanced position, with outer housing distal end 14, as shown in FIG. 3A.

Plunger 34 is slidably and sealingly insertable into outer housing 12. In certain embodiments according to the present invention, first end cap 42 is mounted on ribs 38 and positioned interior to outer housing proximal end 16 such that first end cap 42 is engagable with the inner surfaces of outer housing 12, as shown in FIGS. 1, 3A, and 3C. As shown in FIGS. 1, 2A, 3A, 3B, and 3C, first end cap 42 is generally cylindrical and keyed to elongate rod 36 and one or more ribs 38. In this embodiment of the present invention, outer tissue collection chamber 24 may be defined between outer housing 12, first cylindrical fenestrated member 20, and first end cap 42.

As will be described in more detail below, plunger 34 is axially moveable or slidable within second fenestrated cylindrical member 26 between an advanced position (shown in FIG. 3A) and a retracted position (shown in, for example, FIG. 6A). With reference to FIG. 3A, in the advanced position, plunger rod end 40 is positioned at or near outer housing distal end 14. In operation, the advanced position is achieved by pushing or sliding plunger 34 and, in turn, rod end 40 axially toward outer housing distal end 14. This can be achieved by a user manually operating plunger 34 or can be achieved by automated mechanical means attached to and operating plunger 34. With reference to FIG. 6A, in the retracted position, rod end 40 is positioned near (or as close as possible to) outer housing proximal end 16. In operation, the retracted position is achieved by pulling or sliding plunger 34 and, in turn, rod end 40 axially toward outer housing proximal end 16. This can be achieved by a user manually operating the system or can be achieved by automated mechanical means.

Plunger 34 is also rotatable to, in turn, move or rotate second cylindrical fenestrated member 26 between open and closed positions. In one embodiment, plunger 34 is sealably connected or inserted into second cylindrical fenestrated member 26. Plunger 34 may then be rotated either clockwise or counter clockwise to, in turn, rotate second cylindrical fenestrated member 26 in the same direction. In this embodiment, plunger 34 is engaged with second cylindrical fenestrated member 26 such that second cylindrical fenestrated member 26 moves or rotates upon rotation of plunger 34. This engaging or sealed connection of plunger 34 with second cylindrical fenestrated member 26 can be achieved by direct contact of rod end 40 with the inside surface of second cylindrical fenestrated member 26. This can also be achieved by, for example, second end cap 44 of second cylindrical fenestrated member 26 engaging plunger 34 and second cylindrical fenestrated member 26. Second end cap 44 may be temporarily or permanently fixed to second cylindrical fenestrated member 26, as previously described.

With further reference to FIGS. 1, 2, and 3A, 3B, 3D, 3E, and 3F, tissue or fluid collection system 10 also includes one or more stop units 46 that project from outer housing 12 into outer tissue collection chamber 24, permitting rotation of elongate rod 36 and plunger 34, but restricting rotation of second cylindrical fenestrated member 26 between open and closed positions.

With reference to FIGS. 3A and 3B, in one embodiment, one or more stop units 46 are attached or fixed to outer housing 12 and extend substantially perpendicular to outer housing 12 into outer tissue collection chamber 24. Stop units 46 may be temporarily or permanently attached to outer housing 12. As noted above, one or more stop units 46 are positioned to engage rod 36. In one embodiment, one or more stop units 46 engage ribs 38. One or more stop units 46 may extend to the same or varying radial distances relative to one another. In one embodiment, shown in FIG. 3B, each one or more stop unit 46 extend radially to engage ribs 38.

One or more stop units may be mounted and spaced on outer housing 12 in any suitable manner. In one embodiment, one or more stop units 46 are positioned to restrict rotation of rod 36 and plunger 34 to a particular degree of rotation. For example, system 10 may comprise (a) four stop units 46, allowing about a 90 degree rotation of rod 36 and plunger 34; (b) three stop units, thereby allowing about a 120 degree rotation of rod 36 and plunger 34; (c) two stop units, thereby allowing about a 180 degree rotation of rod 36 and plunger 34; or (d) one stop unit, thereby allowing about a 360 degree rotation of rod 36 and plunger 34. However, it will be understood by those of skill in the art that stop units 46 may be spaced such that approximately about 1 to about 360 degree rotation of rod 36 and plunger 34 is achievable.

With reference to FIG. 3D, one or more stop units 46 may be constructed so that stop units 46 matingly engage ribs 38 and hold second cylindrical fenestrated member 26 in the open or closed positions. For instance, stop units 46 may also comprise stop unit projection 48 that holds ribs 38 in engagement with stop units 46. Stop unit projection 48 may be made of any material, so long as upon application of rotational force to plunger 34 in one direction, stop unit projection 48 permits ribs 38 to slide over stop unit projection 48 and be held in close fitting contact with stop units 46. For example, stop unit projection 48 may be in the form of a flexible material (e.g., plastic, rubber, silicone, etc.) such that upon application of rotational force to plunger 34 in one direction, permits ribs 38 to slide over stop unit projection 48 and be held in close fitting contact with stop units 46. In this embodiment, stop unit projection 48 temporarily holds ribs 38 in close fitting contact with stop units 46 until rotational force is applied to plunger 34 in the opposite direction, allowing ribs to slide over stop unit projection 48 and disengage ribs 38 from stop units 46.

With reference now to FIG. 3E, in one embodiment, stop units 246 are constructed to allow ribs 38 to rotate beyond stop units 246 in one rotational direction, but not in the opposite rotational direction. In this embodiment, stop units 246 may be hinged or may be made of a sufficiently flexible material to allow stop units 246 to bend in one direction (i.e., from position A to B), but not in the opposite direction.

With reference to FIG. 3F, in certain embodiments, at least one of stop units 346 does not engage at least one of ribs 338. This embodiment is also shown in FIG. 5A. This may be achieved by varying the radial projection of at least one of stop units 346 and/or the radial projection of at least one of ribs 338 relative to the remaining stop units 346 and ribs 338, respectively. In one embodiment, stop units 346 extend varying radial distances relative to one another, at least one of one or more stop units 346 does not extend axially to engage ribs 338. In another embodiment, ribs 338 extend to varying radial distances relative to one another, whereby at least one of ribs 338 does not engage stop units 346. As will be understood by those of skill in the art, any combination of such stop units 346 and ribs 338 is contemplated.

As shown in FIGS. 3A, 3B, 3D, and 3E, one or more stop units 46 also serve to temporarily or permanently prevent axial movement (or sliding) of first and/or second cylindrical fenestrated members 20, 26 upon operation of plunger 34 between advanced and retracted positions. Stop units 46 contact first and second cylindrical fenestrated members 20 and 26 such that first and second cylindrical fenestrated members 20 and 26 are not unintentionally displaced from contact with outer housing distal end 14 upon operation of plunger 34. However, in certain embodiments, one or more stop units 46 may be removed or constructed so that they permit removal of first and second cylindrical fenestrated members 20 and 26 upon application of sufficient force.

In certain embodiments according to the present invention, first and/or second cylindrical fenestrated members 20 and 26 are removable from tissue or fluid collection system 10. In this embodiment, plunger 34 is also removed while rod end 40 is sealingly engaged with the interior diameter of second cylindrical fenestrated member 26. In certain embodiments, first and second cylindrical fenestrated members 20 and 26 may both be removed from tissue or fluid collection system 10 together and while rod end 40 of plunger 34 is sealingly engaged with the interior diameter of second cylindrical fenestrated member 26. Removal of both first and second cylindrical fenestrated members 20 and 26 may be while in the closed position and while rod end 40 of plunger 34 is sealingly engaged with the interior diameter of second cylindrical fenestrated member 26. In other embodiments, only second cylindrical fenestrated member 26 and plunger 34 are removed while rod end 40 of plunger 34 is sealingly engaged with the interior diameter of second cylindrical fenestrated member 26. Outer housing 12 at outer housing proximal end 16 and first end cap 42 may be removed to allow removal of first and/or second cylindrical fenestrated members 20 and 26 through outer housing proximal end 16. Stop units 46 may also be removed or may be constructed such that first and/or second cylindrical fenestrated members 20 and 26 may pass by stop units 46 upon application of sufficient force in the direction of outer housing proximal end 16.

With reference now to FIGS. 4A to 4D, it will be understood that one or more stop units 46 may be projections of any form, so long as one or more stop units 46 are sufficiently rigid to temporarily or permanently stop rotation of plunger 34 by engaging ribs 38. For instance, stop units 446 may be projections with blunt ends (as shown in FIG. 4A) or stop units 546 may have rounded ends (as shown in FIG. 4B). Stop units 646 may also be structured to matingly engage ribs 38 upon rotation of plunger 34 in one direction, as shown in FIG. 4C. It will be understood that stop units 746 may also be structured to matingly engage ribs 38 upon rotation of plunger in either direction, as shown in FIG. 4D. It will be understood that in any of these embodiments, stop unit 46 may further include one or more stop unit projections 48, as described above, and may be in any combination.

With continued reference to FIGS. 1, 2, and 3A, tissue collection system 10 may further include outlet 50. Tissue collection system 10 may also include vacuum source 52 coupled to outlet 50. As will be appreciated, vacuum source may be coupled to outlet 50, by e.g., a vacuum or suction line.

With reference to FIGS. 1, 2, 3A, and 3G, tissue collection system 10 may further comprise cannula 54 connected to inlet 18 directly or through conduit 56. As described herein, the term cannula may include needles as a type of cannula. As will be appreciated, cannula 54 may be directly fixed to outer housing 12 and/or inlet 18 by fitting 58 for receiving cannula 54 or conduit 56. Fitting 58 may be, for example, a luer connector.

Referring now to FIGS. 5A-5E, various embodiments of one or more fenestrations 30 and 32 of respective first and second cylindrical fenestrated members 20 and 26 are shown. It will be understood that the embodiments shown may be with respect to either first or second cylindrical fenestrated members 20 and 26. It will also be understood that first cylindrical fenestrated member 20 will have a slightly larger cylindrical diameter than second cylindrical fenestrated member 26. One or more fenestrations 30 and 32 or perforations according to embodiments of present invention may take any shape (e.g., circular, oval, square, etc.) and may be of equal or variable porosity relative to one another. One or more fenestrations 30 and 32 may be distributed in any manner on first and second cylindrical fenestrated members 20 and 26. One or more fenestrations 30 and 32 may be evenly or unevenly distributed on the surfaces of first and second cylindrical fenestrated members 20 and 26. In addition one or more fenestrations may be distributed on surfaces of first and second cylindrical fenestrated members 20 and 26 in any proportion of the surfaces. For instance, one or more fenestrations 30 and 32 on first and second cylindrical fenestrated members 20 and 26 may be distributed on about 1% to about 99% of the surfaces of first and second cylindrical fenestrated members 20 and 26, or any range contained therein. In one embodiment, one or more fenestrations 30 and 32 on first and second cylindrical fenestrated members 20 and 26 are distributed on 5-50% of the surfaces of first and second cylindrical fenestrated members 20 and 26. In other embodiments, one or more fenestrations 30 and 32 on first and second cylindrical fenestrated members 20 and 26 are distributed on up to or at least 5, 10, 15, 20, 25, 30, 35, 40, 45, 50, 55, 60, 65, 70, 75, 80, 85, 90, 95, 96, 97, 98, or 99% of the surfaces of first and second cylindrical fenestrated members 20 and 26.

In certain embodiments, one or more fenestrations 30 and 32 may be distributed in any manner so long as at least one of one or more fenestrations 30 of first cylindrical fenestrated member 20 is capable of being completely or substantially in registration or aligned with at least one of one or more fenestrations 32 of second cylindrical fenestrated member 26 or completely or substantially out of registration (i.e., not aligned), respectively, upon rotation of second cylindrical fenestrated member 26 relative to first cylindrical fenestrated member 20. In one embodiment, first cylindrical fenestrated member 20 has opposed distal end 60 and proximal end 62. Likewise, second cylindrical fenestrated member 26 has opposed distal end 64 and proximal end 66. In certain embodiments, one or more fenestrations 30 and/or 32 may extend along one (FIGS. 5A and 5C) or more (FIG. 5B) linear paths between distal ends 60 and 64 and proximal ends 62 and 66 of first and second cylindrical fenestrated members 20 and 26, respectively.

Figure 5B:
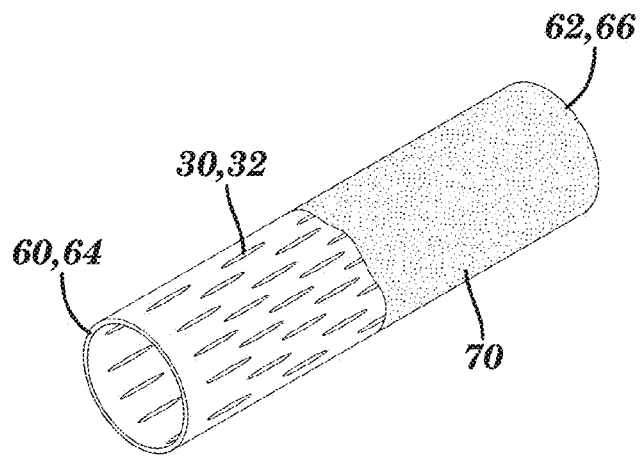
Figure 5C:
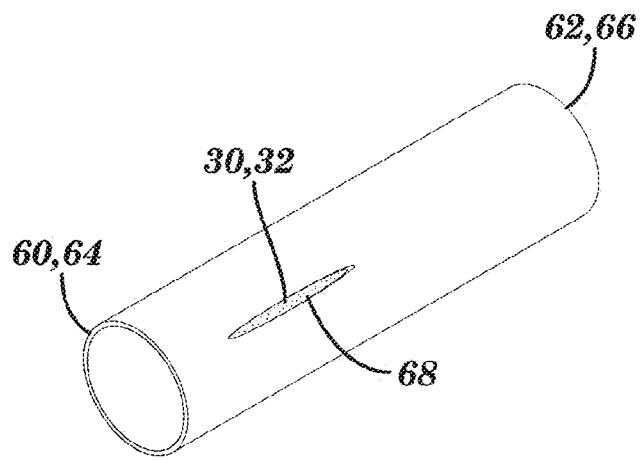

According to certain embodiments of the present invention, one or more fenestrations 30 and/or 32 may comprise additional components such as filter 68, as shown in FIGS. 5B and 5C. Filter 68 may be configured to selectively allow passage of one type of substance through one or more fenestrations 30 and/or 32 and/or to collect that substance on filter 68, while not allowing another type of substance to pass through one or more fenestrations 30 and/or 32 and/or collect on filter 68. Filter 68 may be used for qualitative analytical techniques to determine and identify materials and/or to collect-filter our components. In one embodiment, filter 68 is capable of separating, for example, toxic materials, cancer cells, cells or components based on size, or foreign bodies from tissue or other substance collected. The porosity and material of filter 68 will be determined based on the component being filtered and may range from about 0.1 microns to about 500 microns or, more particularly, from about 5 to about 50 microns. Filter 68 may also have a component bonded to filter 68 in, for example, a gelatinous form that would bond or attract a specific ion or component of the material being filtered. Such filters may also be included within outlet 50 or a vacuum or suction line that interconnects vacuum source 52 to outlet 50, and/or within inlet 18 or conduit 56. In one embodiment, shown in FIG. 5B, filter sleeve 70 may be placed over or circumferentially surrounding first and/or second cylindrical fenestrated members 20 and 26. It will be understood that filter sleeve 70 may be comprised of the same materials and used for the same purposes as described with respect to filter 68. Filter sleeve 70 may replace one of first or second cylindrical fenestrated members 20 and 26 in the system according to the present invention or may be used together with first and second cylindrical fenestrated members 20 and 26. For example, filter sleeve 70 may be positioned between first and second cylindrical fenestrated members 20 and 26 or on either inner or outer side of first and second cylindrical fenestrated members 20 and 26. The system according to the present invention may also comprise more than one filter 68 and/or filter sleeve 70, which may each be made of a different material or have a different porosity than the other(s). Filter 68 or filter sleeve 70 in accordance with embodiments of the present invention may be made of, e.g., mesh-like material and of consistent or variable porosity. Examples of such materials include, but are not limited to, stainless steel mesh or screen, fenestrated Teflon®, nylon mesh or screen, or injection molded polymeric mesh or screen. Filter 68 or filter sleeve 70 in accordance with embodiments of the present invention may be made of, e.g., filter paper.

One or more fenestrations 30 and 32 may be differently distributed on respective first and second cylindrical fenestrated members 20 and 26. For example, first cylindrical fenestrated member 20 may have one or more fenestrations 30 while second cylindrical fenestrated member 26 may comprise, e.g., a single fenestration comprising, e.g., filter 68, as shown in FIG. 5C. The opposite configuration is also contemplated. In another embodiment, each of first and second cylindrical fenestrated members 20 and 26 have a single fenestration comprising, e.g., a filter as described above.

Figure 5D:
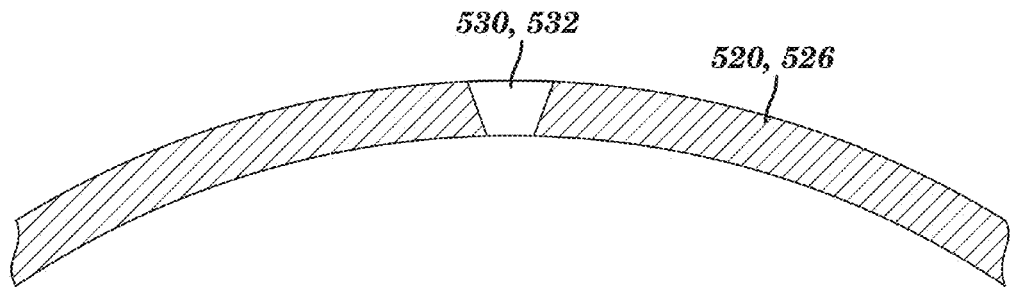
Figure 5E:
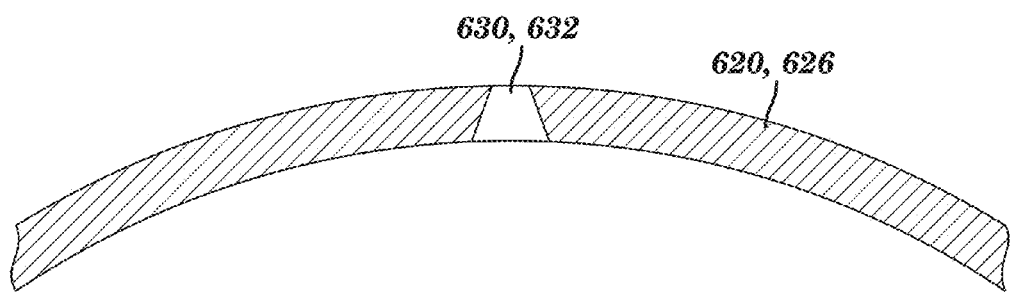

With reference to FIGS. 5D and 5E, one or more fenestrations 30 and/or 32 according to certain embodiments of the present invention may also be of variable porosity. In one embodiment, one or more fenestrations 30 and 32 of first and said second cylindrical fenestrated members 20 and 26, respectively, are wider passing through each one or more fenestrations 30 and 32. For example, the individual one or more fenestrations 30 and/or 32 may be more narrow at the side closest to inner tissue collection chamber 28, i.e., the inlet side, and less narrow (i.e., wider) at the side of the one or more fenestrations closest to outer tissue collection chamber 24, i.e., the outlet side (as shown in FIG. 5D). As shown in FIG. 5E, the opposite configuration is also contemplated.

Tissue collection system 10 according to the present invention may include an inlet sealing means. Referring now to FIGS. 6A to 6E, various embodiments of inlet sealing means in accordance with the present invention are shown. Referring now to FIGS. 6A and 6C, tissue collection system may also include valve 76 proximate to inlet passage 18 to open and close inlet passage 18. As illustrated in FIGS. 6A and 6B, the external portion of valve 76 may be rotated to, in turn, rotate the internal portion of valve 76, sealing inlet 18. As illustrated in FIG. 6C, in another embodiment, valve 676 may be a stopcock-type valve or a push-pull type valve operated by pushing and pulling the external portion of valve 76 to seal and unseal inlet 18. It will be understood that valve 76 may be any valve suitable to close and open inlet passage 18 such as other types of stopcock valves or other valves or sealing means that will be known to those of skill in the art. Examples of such valves include, but are not limited to, three way valves, ball valves, or Tuohy Borst valves.

Referring now to FIGS. 6D and 6E, second cylindrical fenestrated member 626 may include distal end surface 72 having distal end surface opening 74 encompassing a portion of distal end surface 72. In this embodiment, inlet 618 is offset from the center axis of tissue collection system 10 and capable of alignment with distal end surface opening 74. In this embodiment, described in more detail below, distal end surface opening 74 is at least partially covered when second cylindrical fenestrated member 626 is in the open position, but not in the closed position. Thus, when second cylindrical member 626 is in the open position, distal end surface opening 74 is not in alignment with inlet 618, whereby inlet 618 is sealed or covered by distal end surface 72.

Upon partial rotation of second cylindrical fenestrated member 626, distal end surface opening 74 may be partially in alignment with offset inlet passage 618 and second cylindrical fenestrated member 626 will be in a partially open position. Thus, fluid communication between inlet 618, inner tissue collection chamber 28, and outer tissue collection chamber 24 is achieved in this position. Such fluid communication may also be achieved when second cylindrical fenestrated member 26 is in the open position and inlet 18 is not sealed by other inlet sealing means, e.g., valve 76 or cap 78 (shown in FIGS. 6B-6C and 6F, respectively). This fluid communication may be useful for a number of purposes, including drawing additional tissue or other substances (e.g., washing liquid or other tissue additives or enhancers) through inlet 618, inner tissue collection chamber 28, one or more fenestrations 30, and outer tissue collection chamber 24.

Tissue collection system 10 may also include removable cap 78 to seal and cover inlet 18, as shown in FIG. 6F.

According to embodiments of the present invention, components of the tissue collection system 10 according to the present invention (e.g., outer housing 12, first cylindrical fenestrated member 20, second cylindrical fenestrated member 26, plunger 34, and one or more stop units 46) may be formed of a substantially rigid material capable of withstanding vacuum pressure when applied to the system. Suitable substantially rigid materials are well known to those of skill in the art. For example, the substantially rigid material may be any one or more of plastic, polymers, rubber materials, metals, alloys, glass, quartz, ceramics, or any combination thereof. In other embodiments, first and/or second cylindrical fenestrated members 20 and 26 may be made of a mesh material and be in the form of a sleeve that may or may not be substantially rigid. Examples of such mesh materials include, but are not limited to, stainless steel mesh or screen, fenestrated Teflon®, nylon mesh or screen, or injection molded polymeric mesh or screen.

It will be understood that the system according to the present invention may be used to collect and/or filter or separate any fluid, viscous, semi-solid, or solid. This includes any type of body tissue that requires collection, aspiration, washing, and/or separation of its components. In one embodiment, the system according to the present invention is used to collect, aspirate, wash, and/or separate a tissue sample that comprises fat. The system according to the present invention may also be used for biopsying solid or semi-solid organ tissue and provide the ability to concentrate samples from any type of fluid collection including infectious, oncologic, traumatic, or benign. For example, in another embodiment, the tissue sample comprises bone marrow. In certain embodiments, the fenestrations or mesh material has (or have) a porosity level to allow the passage of fluid but not cellular sized particles.

Another aspect of the present invention relates to a method for separating components of a tissue sample. The method includes providing a system comprising an outer housing having opposed distal and proximal ends, where the distal end is provided with an inlet passage. A first cylindrical fenestrated member is within and immovable relative to the outer housing, where an outer tissue collection chamber is defined between the outer housing and the first cylindrical fenestrated chamber. A second cylindrical fenestrated member defines an inner tissue collection chamber and is positioned within and rotatable relative to the first cylindrical fenestrated member between an open position and a closed position. In the open position, the fenestrations of the first cylindrical fenestrated member and the fenestrations of the second cylindrical fenestrated member are in registration with one another, thereby permitting fluid communication between the inner tissue collection chamber and the outer tissue collection chamber. In the closed position, the fenestrations of the first cylindrical fenestrated member and the fenestrations of the second cylindrical fenestrated member are not in registration with one another, thereby preventing fluid communication between the inner tissue collection chamber and the outer tissue collection chamber. A plunger is axially movable within the second fenestrated cylindrical member between an advanced position near the distal end of the outer housing and a retracted position near the proximal end of the outer housing. The plunger is rotatable to move the second cylindrical fenestrated member between the open and closed positions. An elongate rod having a plurality of longitudinally-extending ribs is connected to the plunger to move the plunger axially between the advanced and retracted positions, and extends through the proximal end of the outer housing. One or more stop units are attached to the outer housing, extending into the outer tissue collection chamber, and positioned to engage the ribs, permitting rotation of the rod and the plunger but restricting rotation of the second cylindrical fenestrated member between the open and closed positions. The method also includes placing the inlet in contact with the fluid sample with the plunger in the advanced position and the first and second cylindrical fenestrated members in the closed position. The plunger is then moved with the rod to the retracted position to draw the fluid sample into the inner tissue collection chamber.

Operation of tissue collection system 10 is best described with reference to FIGS. 7 to 9.

Figure 7A:
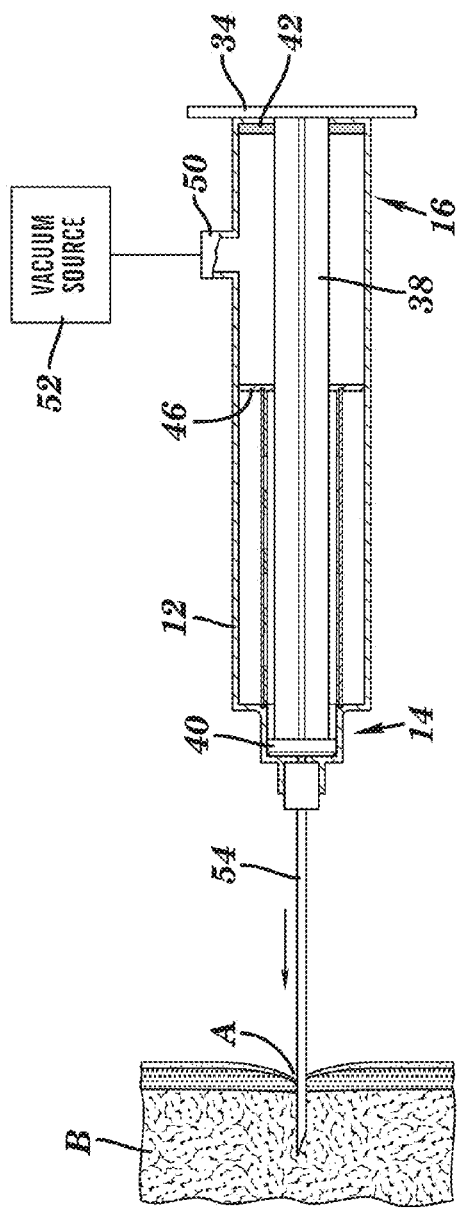
FIGS. 7A to 7H are a series of schematic cross-sectional views illustrating operation of a tissue collection system according to the present invention.
Figure 7B:
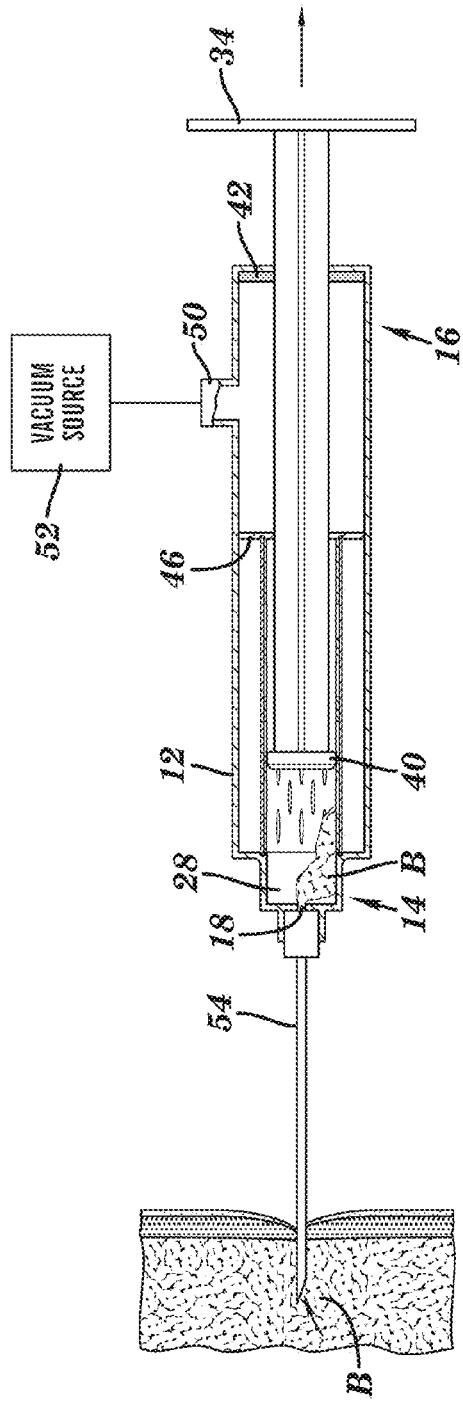

Referring now to FIG. 7A and 7B, with plunger 34 in the advanced position and second cylindrical fenestrated member 26 in the closed position, tissue collection system 10 is placed in contact with penetration site A and forced to penetrate into donor site comprising tissue B (e.g., fat tissue). With reference to FIG. 7B, plunger 34 is moved to the retracted position, drawing tissue B through inlet passage 18 and into inner tissue collection chamber 28.

Figure 7C:
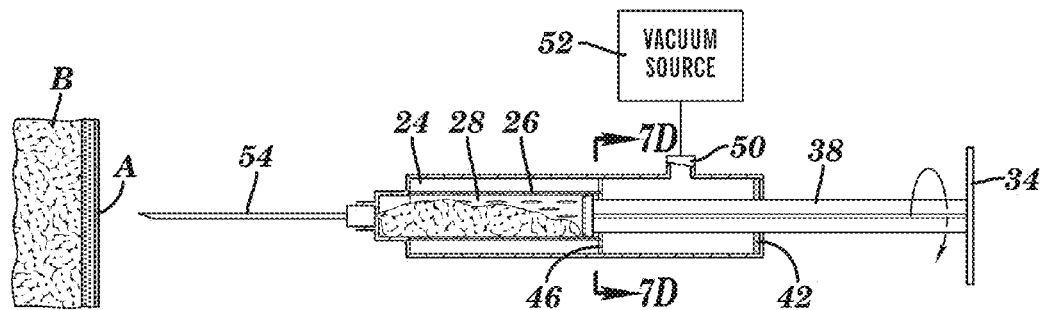
Figure 7D:
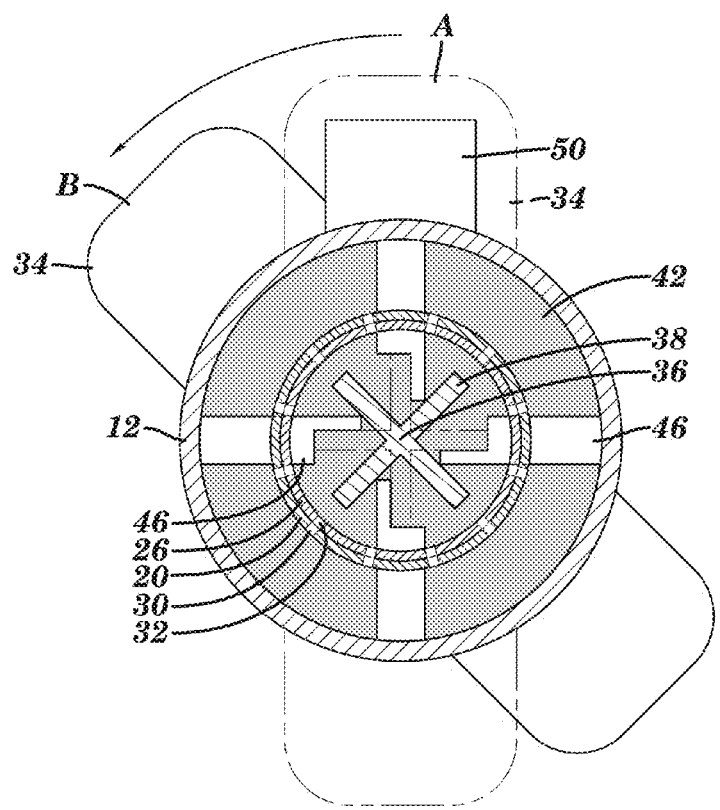

With reference to FIG. 7C, tissue collection system 10 is then withdrawn from penetration site A. Now with reference to FIGS. 7C and 7D, once in the retracted position, plunger 34 is rotated. As shown in FIG. 7D, rotation of plunger 34, in turn, rotates second cylindrical fenestrated member 26 from the closed (A) to the open position (B). Rotation is stopped when ribs 38 engage stop units 46 (FIG. 7D). As noted above, in the open position, fluid communication between inner tissue collection chamber 28 and outer tissue collection chamber 24 is achieved.

Figure 7E:
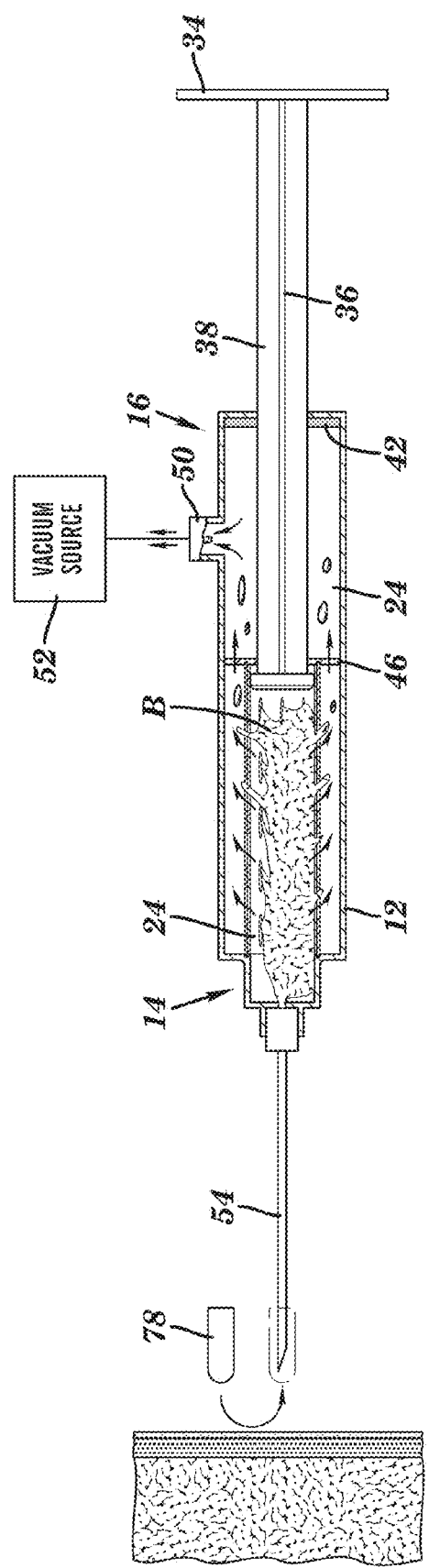

Referring now to FIG. 7E, inlet 18 is then sealed by application of cap 78 to cannula 54. As will be apparent, various inlet sealing means known to those of skill in the art, including those described in the present application, will be effective in sealing inlet 18. Once inlet 18 is sealed, negative pressure is applied to tissue collection system 10, separating components of tissue sample B. After sealing inlet 18, negative pressure is applied to tissue collection system 10 through outlet 50 by vacuum source 52. At least a portion of tissue B (e.g., fat) will be retained in inner tissue collection chamber for, e.g., reinjection at an alterative body site and/or washing steps, while other fluids (e.g., blood, serum, undesirable components, etc.) are drawn through fenestrations 30 and 32 and into outer tissue collection chamber 24. Components drawn into outer tissue collection chamber 24 may also be removed through outlet 50 by operation of vacuum source 52 or other negative pressure means.

It will be understood by those of skill in the art that system 10 may be used for washing the contents of inner tissue collection chamber 28. This may be accomplished by, for example, unsealing inlet 18 while second cylindrical fenestrated member 26 is in the open position and drawing a washing or other liquid into inner tissue collection chamber through inlet passage 18 by applying vacuum source 52 or other negative pressure means to outlet 50. Washing can be carried out to clean, enhance, or supplement (e.g., by application of growth factors, antibodies, stem cells, virus, signal blockers (e.g., siRNA), signal enhancers, etc.) tissue sample B. Washing may be used to prepare tissue sample B for reinjection at the same or another body site. The system and methods according to the present invention may also be used, for example, for scientific/laboratory specimen collection to, e.g., purify cell collections.

In certain embodiments according to the present invention, first and/or second cylindrical fenestrated members 20 and 26 may be removed from tissue or fluid collection system 10. In this embodiment, plunger 34 is also removed while rod end 40 is sealingly engaged with the interior diameter of second cylindrical fenestrated member 26. In certain embodiments according to the present invention, first and second cylindrical fenestrated members 20 and 26 may both be removed from tissue or fluid collection system 10 while in the closed position and while rod end 40 of plunger 34 is sealingly engaged with the interior diameter of second cylindrical fenestrated member 26. In another embodiment, only second cylindrical fenestrated member 26 and plunger 34 are removed while rod end 40 of plunger 34 is sealingly engaged with the interior diameter of second cylindrical fenestrated member 26. Removal of first and/or second cylindrical fenestrated members 20 and 26 may be once tissue or fluid is collected in inner tissue collection chamber 28 and before or after a vacuum source is applied. In this way, tissue or fluid collected in inner tissue collection chamber 28 may be emptied, transported, stored, processed, etc. In one embodiment, first and/or second cylindrical fenestrated members 20 and 26 are removed and replaced by replacement first and/or second cylindrical fenestrated members 20 and 26. In certain embodiments, replacement first and/or second cylindrical fenestrated members 20 and 26 contain tissue suitable for injection into a subject. In one embodiment, replacement first and second cylindrical fenestrated members 20 and 26 are in the closed position.

Figure 7F:
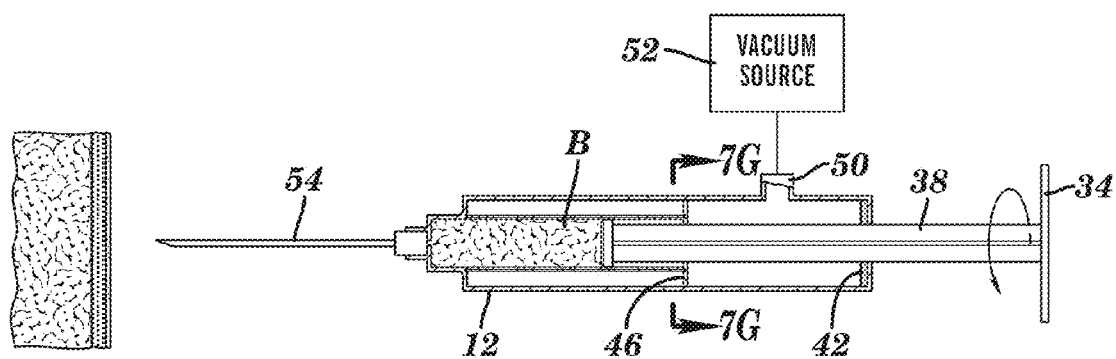
Figure 7G:
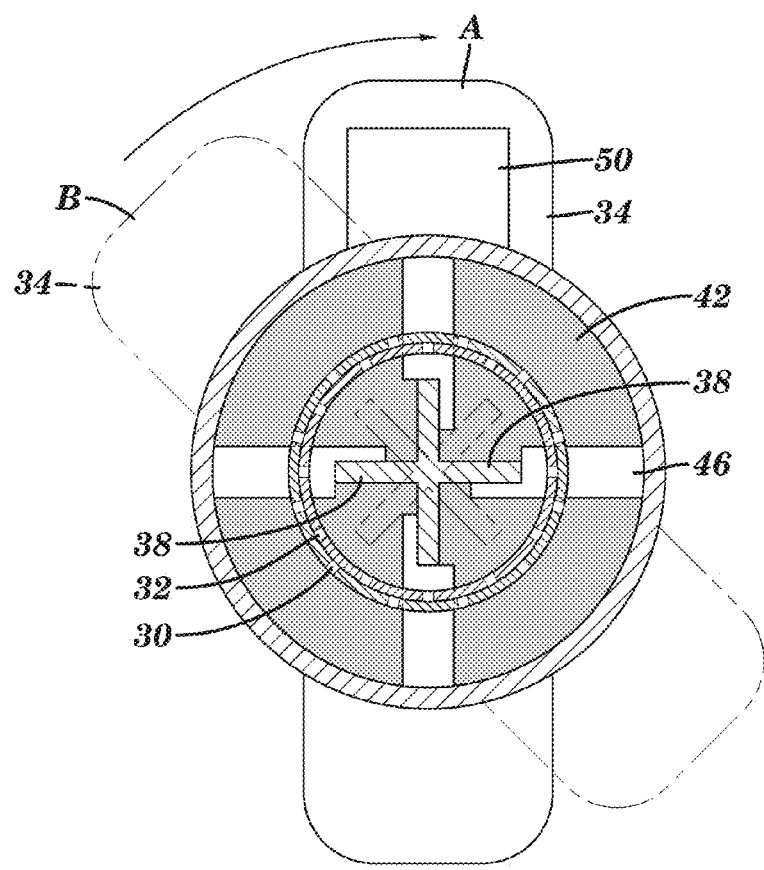

With reference to FIG. 7F, after desired separation of tissue is complete, vacuum source 52 is stopped or removed. Tissue collection system 10 is then prepared for use in reinjection of components remaining in inner tissue collection chamber after separation and/or washing. With reference to FIG. 7G, this is accomplished by rotating plunger 34 and, in turn, second cylindrical fenestrated member 26, from the open (B) to the closed (A) position. As shown in FIG. 7G, as plunger 34 is rotated, ribs 38 will engage stop units 46 once second cylindrical fenestrated member 26 is in the closed position (A). As noted above, in the closed position, fluid communication between inner tissue collection chamber 28 and outer tissue collection chamber 24 is prevented.

Figure 7H:
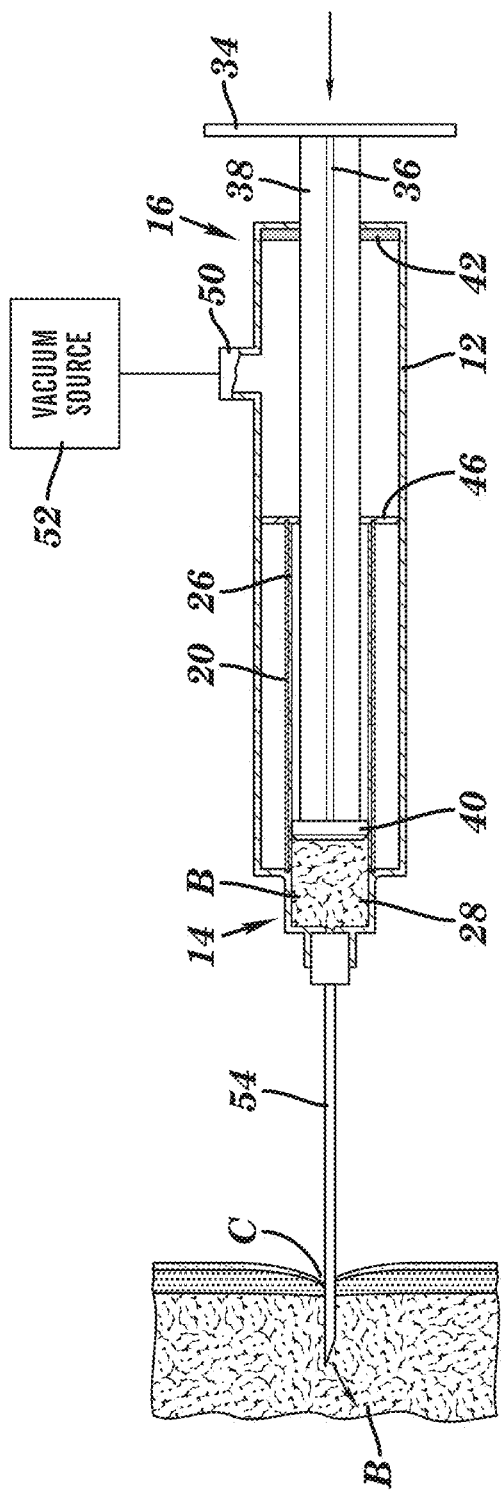

As shown in FIG. 7H, syringe or cannula 54 then penetrates the same or alternative penetration site C on a subject, and plunger 34 is moved to the advanced position, expelling at least a portion of tissue sample B that remains in inner tissue collection chamber 28 into the subject. This may occur in the same procedure as the removal of tissue B or at a later time, e.g., during a separate procedure.

Figure 8C:
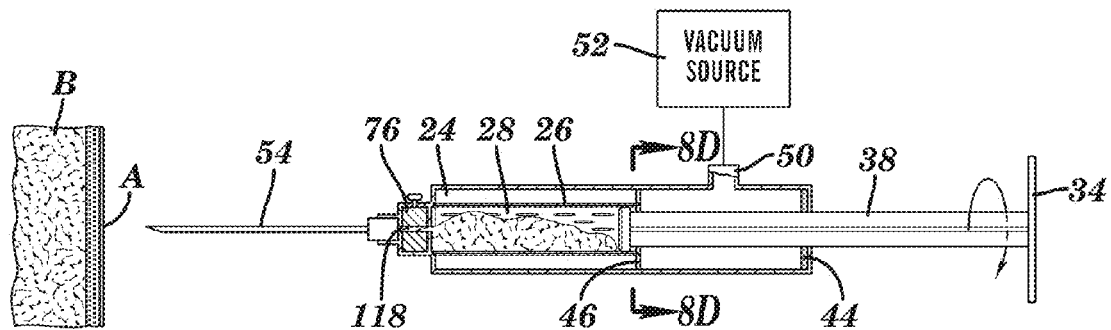
Figure 8D:
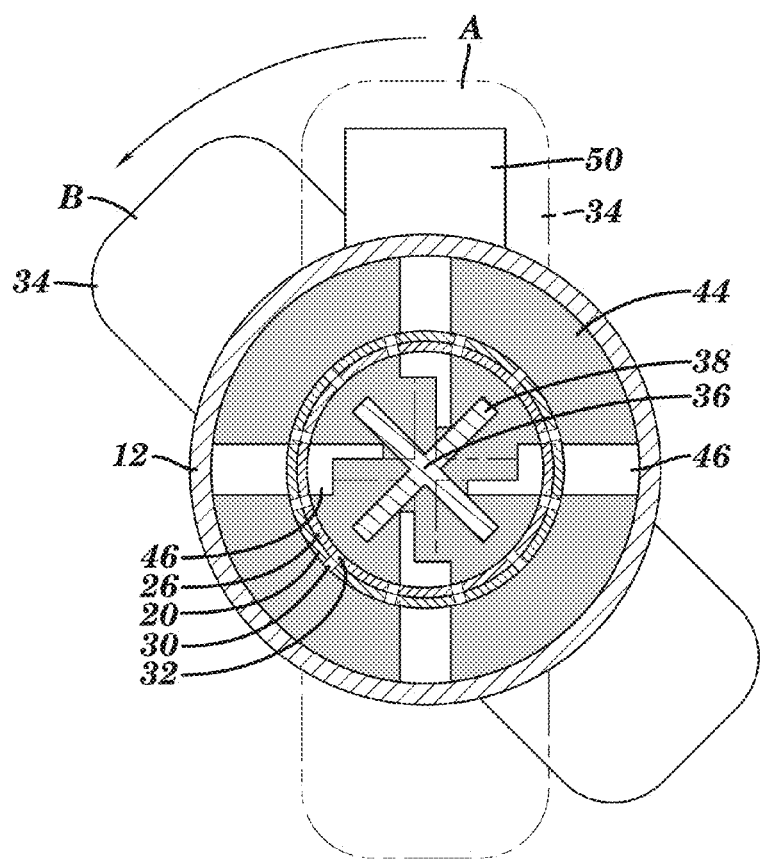

With reference to FIGS. 8A to 8J, operation of an embodiment of tissue collection system 10 is shown with an alternative sealing means. With reference to FIG. 8A, as described above, tissue collection system 10 that includes a valve sealing means 76 is placed in contact with penetration site A and forced to penetrate into donor site comprising tissue B (e.g., fat tissue). In FIG. 8B, plunger 34 is then moved to the retracted position, drawing tissue B through inlet passage 118 and into inner tissue collection chamber 28. As described above and is shown in FIGS. 8C and 8D, rotation of plunger 34, in turn, rotates second cylindrical fenestrated member 26 from the closed (A) to the open position (B). Rotation is stopped when ribs 38 engage stop units 46 (FIG. 8D). As noted above, in the open position, fluid communication between inner tissue collection chamber 28 and outer tissue collection chamber 24 is achieved.

With reference now to FIG. 8E and 8F, inlet 118 is sealed by operating a valve sealing means. As shown in FIGS. 8E and 8F, a rotating valve 76 sealing means may be operated by rotating an external portion of valve 76, which, in turn, rotates and internal portion of valve 76 thereby sealing or closing inlet 118. In another embodiment, shown in FIG. 8G, the valve sealing means is a stop-cock or push-pull type valve 876, which is operated by pushing and/or pulling an external portion of valve 876, thereby sealing inlet 118.

As shown in FIGS. 8E and 8G, once inlet 118 is sealed, negative pressure is applied to tissue collection system 10, separating components of tissue sample B. Negative pressure can be applied to tissue collection system 10 through outlet 50 by vacuum source 52, separating tissue B, as described in detail above.

Figure 8H:
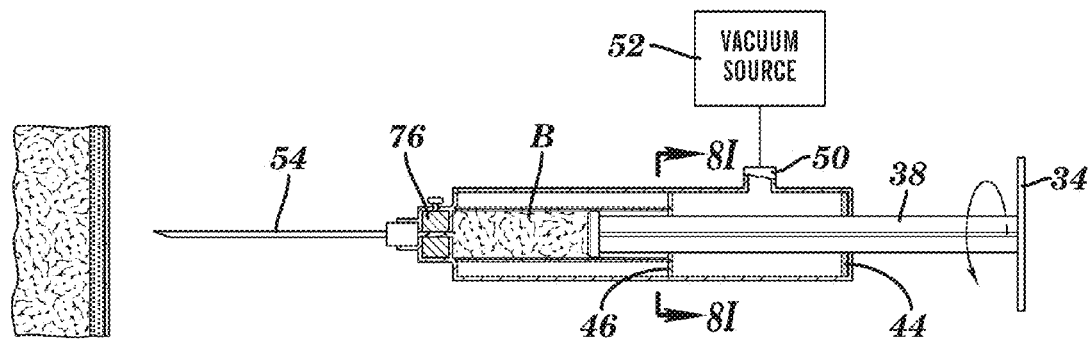
Figure 8I:
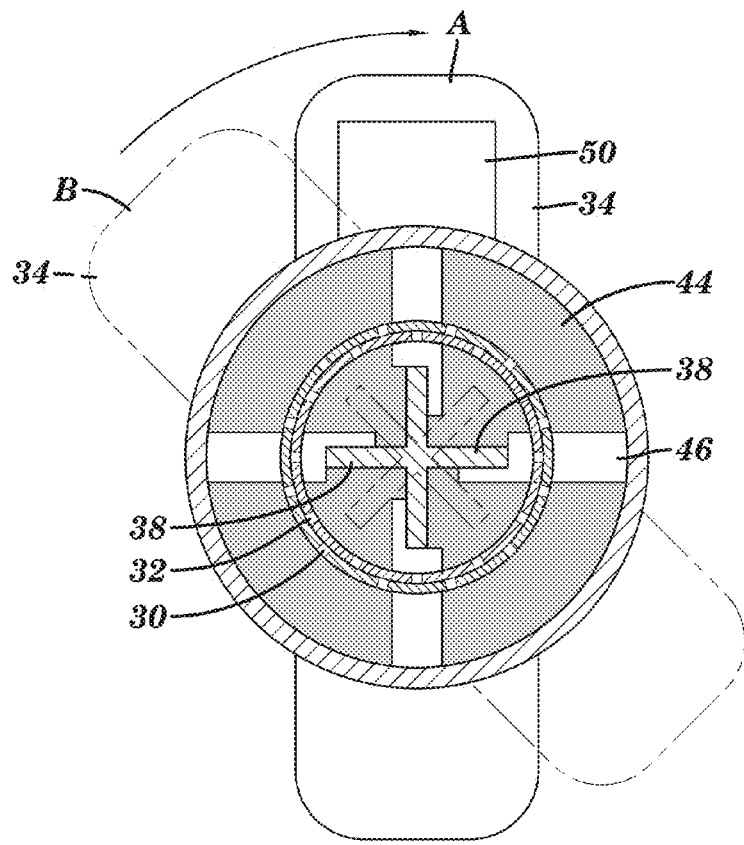

Now referring to FIGS. 8H and 8I, tissue collection system 10 is then prepared for use in reinjection of components remaining in inner tissue collection chamber after separation and/or washing. With reference to FIG. 8H, this is accomplished by rotating plunger 34 and, in turn, second cylindrical fenestrated member 26, from the open (B) to the closed (A) position. As shown in FIG. 8I, as plunger 34 is rotated, ribs 38 will engage stop units 46 once second cylindrical fenestrated member 26 is in the closed position (A). As noted above, in the closed position, fluid communication between inner tissue collection chamber 28 and outer tissue collection chamber 24 is prevented.

Figure 8J:
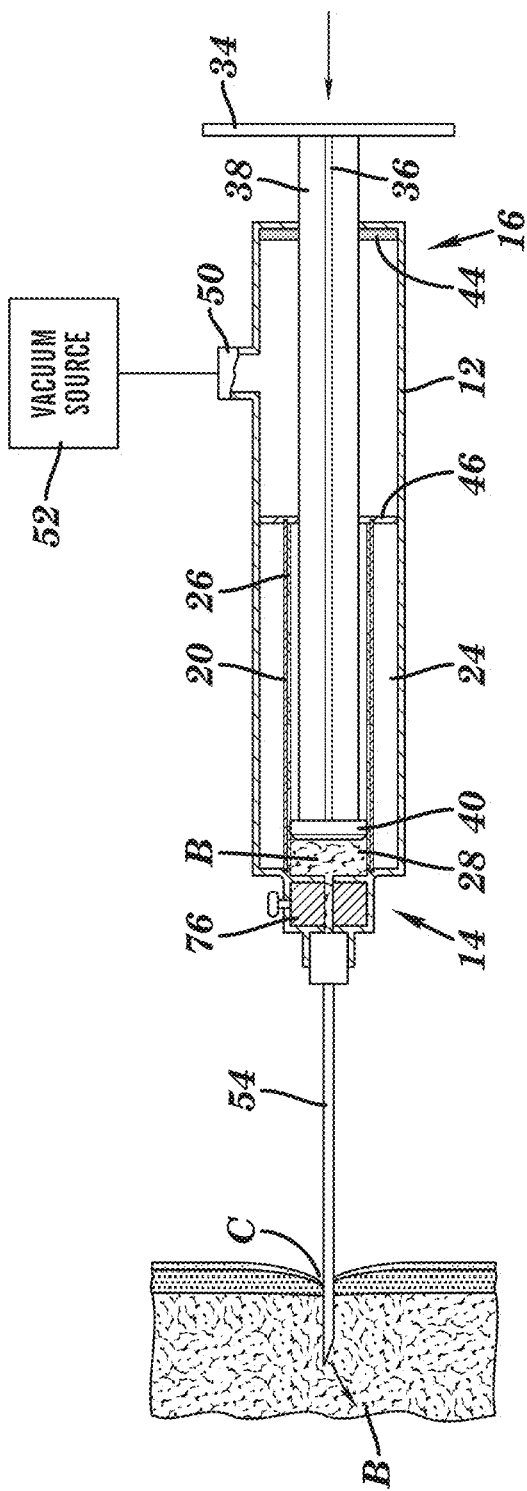

With reference to FIG. 8J, syringe or cannula 54 then penetrates the same or alternative penetration site C in a subject, and plunger 34 is moved to the advanced position, expelling at least a portion of tissue sample B that remains in inner tissue collection chamber 28 into the subject. This may occur in the same procedure as the removal of tissue B or at a later time, e.g., during a separate procedure.

Figure 9D:
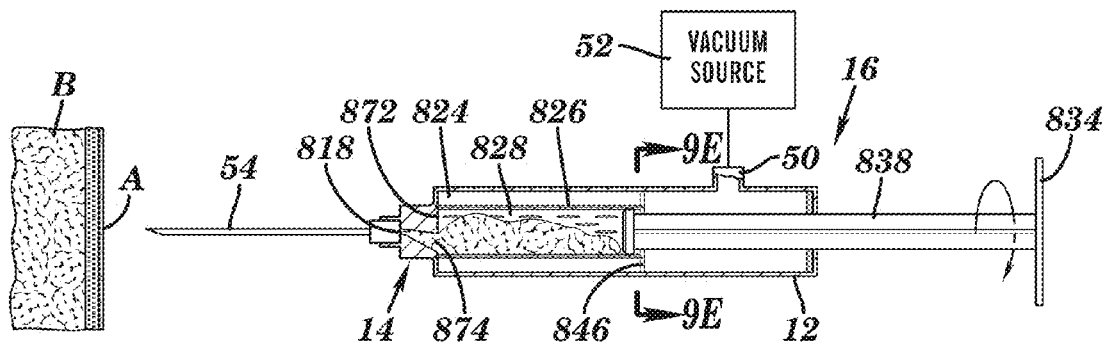

Referring now to FIGS. 9A to 9J, another embodiment according to the present invention that includes an alternative inlet sealing means is shown in use. As shown in FIGS. 9A and 9B, in this embodiment, inlet 818 is offset from the center axis of tissue collection system 10 and capable of substantial or complete alignment with distal end surface opening 874 when second cylindrical fenestrated member 826 is in the closed position. This permits passage of tissue B through inlet 818 upon sliding plunger 834 to the retracted position, as shown in FIGS. 9A and 9B.

With reference to FIG. 9C, in this embodiment, at least two ribs 838 contact at least two stop units 846. This may be accomplished by varying the lengths of stop units 846 and/or ribs 838. This may also be accomplished by a tissue collection system that comprises only two stop units 846 and only two ribs 838.

Figure 9E:
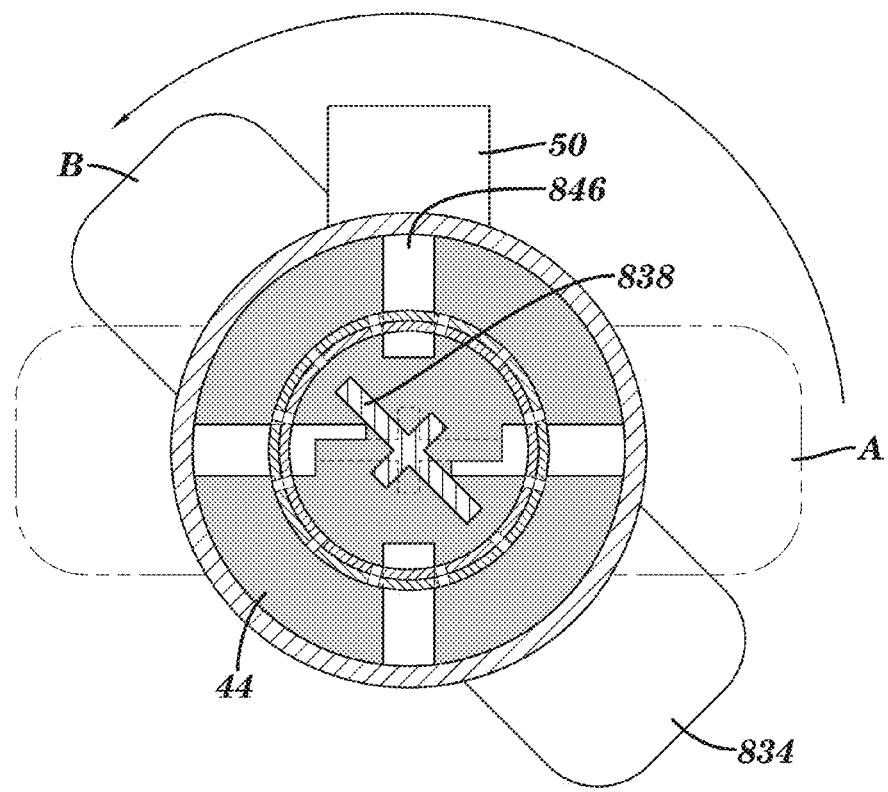

With reference now to FIG. 9D and 9E, after tissue B is within inner tissue collection chamber 828, inlet 818 is then sealed by rotation of plunger 834 and, in turn, second cylindrical fenestrated member 826 to the open position. Upon rotation of plunger 834 and, in turn, second cylindrical fenestrated member 826 is rotated to the open position, inlet 818 and distal end surface opening 874 are not aligned and inlet 818 is covered by distal end surface 872, thereby sealing inlet 818. As shown in FIGS. 9F and 9G, once inlet 818 is sealed, vacuum source 52 is applied to outlet 50 and components of tissue sample B are separated in the same manner as described above.

As shown in FIGS. 9C and 9E, ribs 838 and stop units 846 may be configured to permit rotation of plunger 834 and, in turn, rotation of second cylindrical fenestrated member 826 between at least two positions, one in which the inlet 818 is aligned with distal end surface opening 874 and one in which inlet 818 is sealed or not aligned with distal end surface opening 874. For example, in one embodiment, one or more stop units 846 are position to allow up to an approximate 90 or 180 degree rotation of plunger 834 and, in turn, rotation of second cylindrical fenestrated member 826.

As described above, upon partial rotation of second cylindrical fenestrated member 826, distal end surface opening 874 may be partially in alignment with offset inlet passage 518 and, thereby, second cylindrical fenestrated member 826 will be in a partially open position. Thus, fluid communication between inlet 818, inner tissue collection chamber 828, and outer tissue collection chamber 824 is achieved in this position. In this way, a completely open system is achieved permitting the intake of a washing liquid or enhancer or treatment fluid (described above) through inlet 818 by applying negative pressure to the system through outlet 52.

Figure 9H:
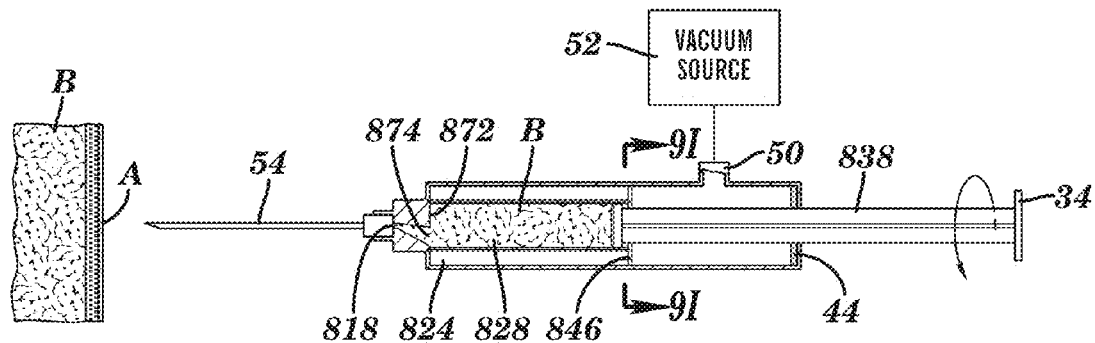
Figure 9I:
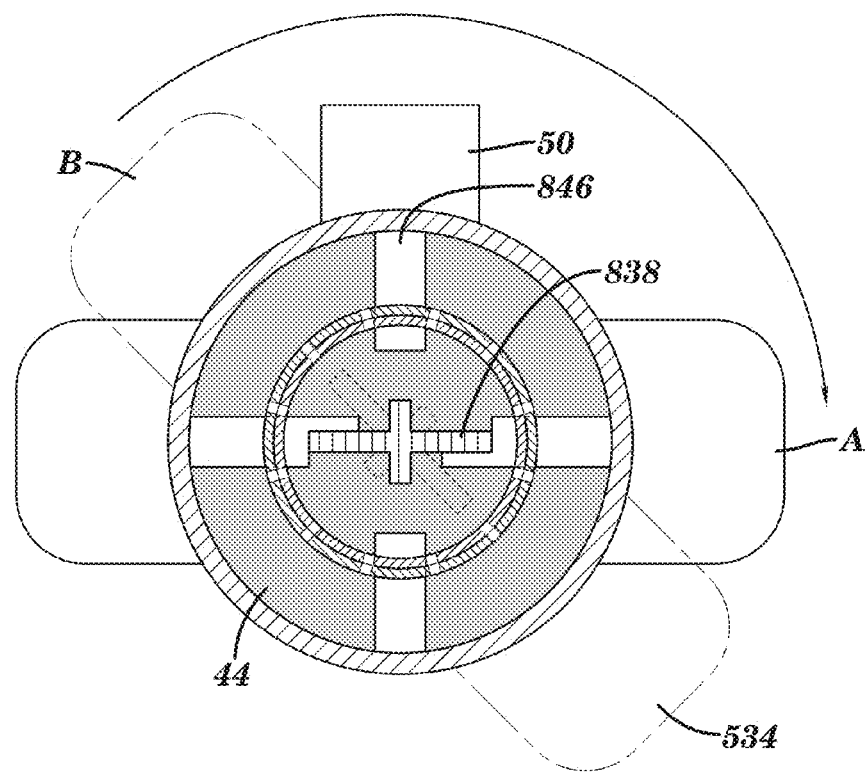

As described above and with reference now to FIGS. 9H and 9I, after desired separation/washing/treating of tissue is complete, vacuum source 52 is stopped or removed. Tissue collection system 10 is then prepared for use in reinjection of components remaining in inner tissue collection chamber 828 after separation and/or washing. As shown in FIGS. 9H and 9I, this is accomplished by rotating plunger 834 and, in turn, second cylindrical fenestrated member 826, to the closed position. As shown in FIG. 9I, as plunger 834 is rotated, ribs 838 will engage stop units 846 once second cylindrical fenestrated member 826 is in the closed position. As noted above, in the closed position, fluid communication between inner tissue collection chamber 828 and outer tissue collection chamber 824 is prevented.

Figure 9J:
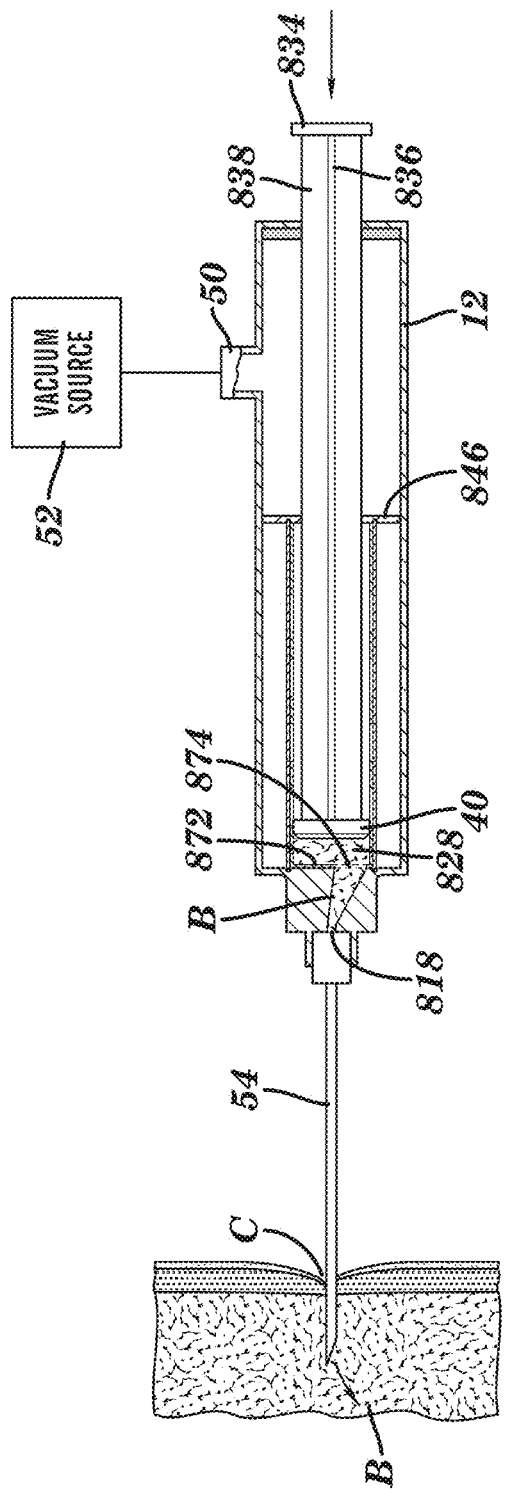

With reference to FIG. 9J, syringe or cannula 854 may then penetrate the same or alternative penetration site C on a subject, and plunger 834 is moved to the advanced position, expelling at least a portion of tissue sample B that remains in inner tissue collection chamber 828 into the subject.

As can be appreciated by one of skill in the art, the tissue collection system described can be made of any suitable material known to those of skill in the art and can be made to be disposable (i.e., not for reuse) or sterilizable and intended for reuse.

Although the invention has been described in detail for the purposes of illustration, it is understood that such detail is solely for that purpose, and variations can be made therein by those skilled in the art without departing from the spirit and scope of the invention which is defined by the following claims.

What is claimed:

1. A tissue collection system comprising:
an outer housing having opposed distal and proximal ends, wherein said distal end is provided with an inlet passage;
a first cylindrical fenestrated member within and immovable relative to said outer housing, wherein an outer tissue collection chamber is defined between said outer housing and said first cylindrical fenestrated member;
a second cylindrical fenestrated member defining an inner tissue collection chamber and being positioned within and rotatable relative to said first cylindrical fenestrated member between an open position in which the fenestrations of said first cylindrical fenestrated member and the fenestrations of said second cylindrical fenestrated member are in registration with one another, thereby permitting fluid communication between the inner tissue collection chamber and the outer tissue collection chamber, and a closed position in which the fenestrations of said first cylindrical fenestrated member and the fenestrations of said second cylindrical fenestrated member are not in registration with one another, thereby preventing fluid communication between the inner tissue collection chamber and the outer tissue collection chamber;
a plunger axially movable within said second cylindrical fenestrated member between an advanced position near the distal end of said outer housing and a retracted position near the proximal end of said outer housing, said plunger being rotatable to move said second cylindrical fenestrated member between the open and closed positions;
an elongate rod being connected to said plunger to move said plunger axially between the advanced and retracted positions, and extending through the proximal end of said outer housing, wherein said elongate rod comprises a plurality of longitudinally-extending ribs;
and one or more stop units attached to the interior surface of said outer housing, extending into the outer tissue collection chamber, and wherein at least one of said one or more stop units is positioned to engage said ribs, wherein at least a portion of at least one of said one or more stop units is positioned proximal to said first and second cylindrical fenestrated members to limit axial movement of said first and second cylindrical fenestrated members to positions proximal of the at least one of said one or more stop units, and wherein rotation of said rod and said plunger rotates said second cylindrical fenestrated member between the open and closed positions, and wherein at least one of said one or more stop units engage at least one of said ribs at the open position and at the closed position.

2. The system of claim 1 further comprising:
an outlet operatively coupled to said outer housing.

3. The system of claim 2 further comprising:
a vacuum source coupled to said outlet.

4. The system of claim 1, wherein the fenestrations are evenly distributed on surfaces of said first cylindrical fenestrated member and said second cylindrical fenestrated member.

5. The system of claim 4, wherein the fenestrations are distributed on 5-50% of the surfaces of said first cylindrical fenestrated member and said second cylindrical fenestrated member.

6. The system of claim 1, wherein the fenestrations are unevenly distributed on surfaces of said first cylindrical fenestrated member and said second cylindrical fenestrated member.

7. The system of claim 6, wherein the fenestrations are distributed on 5-50% of the surfaces of said first cylindrical fenestrated member and said second cylindrical fenestrated member.

8. The system of claim 1, wherein the fenestrations of said first cylindrical fenestrated member and said second cylindrical fenestrated member are of variable porosity.

9. The system of claim 1, wherein the fenestrations of said first cylindrical fenestrated member and said second cylindrical fenestrated member widen passing through each fenestration.

10. The system of claim 6, wherein said first and said second cylindrical fenestrated members have opposed distal and proximal ends and the fenestrations on said first and said second cylindrical fenestrated members extend along one or more linear paths between said distal and said proximal ends of said first and second cylindrical fenestrated members, respectively.

11. The system of claim 1, wherein at least one of said fenestrations further comprises a filter.

12. The system of claim 1, wherein said outer housing, said first cylindrical fenestrated member, said second cylindrical fenestrated member, and said rod are made from plastic, polymers, rubber materials, metals, alloys, glass, quartz, ceramics, or mixtures thereof.

13. The system of claim 1 further comprising:
a cannula and
a conduit coupling said cannula to the inlet.

14. The system of claim 1, wherein there are either: (a) four stop units, allowing about a 90 degree rotation of said rod and said plunger; (b) three stop units, thereby allowing about a 120 degree rotation of said rod and said plunger; (c) two stop units, thereby allowing about a 180 degree rotation of said rod and said plunger; or (d) one stop unit, thereby allowing about a 360 degree rotation of said rod and said plunger.

15. The system of claim 1, wherein said elongate rod has 1, 2, 3, or 4 ribs.

16. The system of claim 1, wherein the plurality of longitudinally-extending ribs extend varying radial distances relative to one another, whereby at least one rib does not engage said stop units.

17. The system of claim 1, wherein the plurality of longitudinally-extending ribs extend the same radial distances relative to one another, whereby all of the plurality of longitudinally-extending ribs engage said stop units.

18. The system of claim 1, wherein the ribs and said stop units are constructed so that the ribs rotate beyond said stop units in one rotational direction, but not in the opposite rotational direction.

19. The system of claim 1, wherein the ribs and said stop units are constructed so that said stop units matingly engage the ribs and hold said second cylindrical fenestrated member in the open or closed position.

20. The system of claim 1 further comprising:
a first end cap mounted on the ribs of said rod and engageable with inner surfaces of said outer housing near its proximal end; and
a second end cap to seal the inner tissue collection chamber at a location spaced from the inlet.

21. The system of claim 20, wherein said second cylindrical fenestrated member has a distal end surface which has an opening encompassing a portion of the end surface, said opening being at least partially covered when said second cylindrical fenestrated member is in the open position but not in the closed position.

22. The system of claim 1 further comprising:
a valve proximate to the inlet to open and close the inlet.

23. The system of claim 1 further comprising:
an inlet cap to seal and cover the inlet.

24. A method for separating components of tissue sample comprising:
providing a system comprising:
an outer housing having opposed distal and proximal ends, wherein said distal end is provided with an inlet passage;
a first cylindrical fenestrated member within and immovable relative to said outer housing, wherein an outer tissue collection chamber is defined between said outer housing and said first cylindrical fenestrated member;
a second cylindrical fenestrated member defining an inner tissue collection chamber and being positioned within and rotatable relative to said first cylindrical fenestrated member between an open position in which the fenestrations of said first cylindrical fenestrated member and the fenestrations of said second cylindrical fenestrated member are in registration with one another, thereby permitting fluid communication between the inner tissue collection chamber and the outer tissue collection chamber, and a closed position in which the fenestrations of said first cylindrical fenestrated member and the fenestrations of said second cylindrical fenestrated member are not in registration with one another, thereby preventing fluid communication between the inner tissue collection chamber and the outer tissue collection chamber;
a plunger axially movable within said second cylindrical fenestrated member between an advanced position near the distal end of said outer housing and a retracted position near the proximal end of said outer housing, said plunger being rotatable to move said second cylindrical fenestrated member between the open and closed positions;
an elongate rod being connected to said plunger to move said plunger axially between the advanced and retracted positions, and extending through the proximal end of said outer housing, wherein said elongate rod comprises a plurality of longitudinally-extending ribs; and
one or more stop units attached to the interior surface of said outer housing, extending into the outer tissue collection chamber, wherein at least one of said one or more stop units is positioned to engage at least one of said ribs, wherein at least a portion of at least one of said one or more stop units is positioned proximal to said first and second cylindrical fenestrated members to limit axial movement of said first and second cylindrical fenestrated members to positions proximal of the at least one of said one or more stop units, and wherein rotation of said rod and said plunger rotates said second cylindrical fenestrated member between the open and closed positions, and wherein at least one of said one or more stop units engage at least one of said ribs at the open position and at the closed position;

placing the inlet in contact with the tissue sample with said plunger in the advanced position and said second cylindrical fenestrated member in the closed position; and moving said plunger with said rod to the retracted position to draw the tissue sample into the inner tissue collection chamber.

25. The method according to claim 24 further comprising:
sealing the inlet after said moving;
rotating said second cylindrical fenestrated member with said rod to position the second cylindrical fenestrated member in the open position; and
applying negative pressure to the outer tissue collection chamber to draw the tissue sample from the inner tissue collection chamber to the outer tissue collection chamber.

26. The method of claim 24 further comprising:
providing an outlet operatively coupled to the outer housing to permit fluid communication between the outer housing's outer periphery and the outer tissue collection chamber and
withdrawing the tissue sample from the outer housing through the outlet after said applying negative pressure.

27. The method of claim 26, wherein said withdrawing is carried out with a vacuum operatively coupled to the outlet.

28. The method of claim 24, wherein said system further comprises:
a cannula operatively connected to the inlet, through which tissue passes during said moving.

29. The method of claim 28, wherein the system further comprises:
a conduit coupling said cannula to the inlet.

30. The method according to claim 25 further comprising:
rotating said second cylindrical fenestrated member relative to said first cylindrical fenestrated member such that said second cylindrical fenestrated member is in the closed position and a portion of the tissue sample is retained in the inner tissue collection chamber, and
ejecting at least a portion of tissue sample retained in said inner tissue collection chamber through the inlet passage by moving the plunger to the advanced position.

31. The method of claim 24, wherein said tissue sample comprises fat.

32. The method of claim 24, wherein the fenestrations are evenly distributed on surfaces of said first cylindrical fenestrated member and said second cylindrical fenestrated member.

33. The method of claim 32, wherein the fenestrations are distributed on 5-50% of the surfaces of said first cylindrical fenestrated member and said second cylindrical fenestrated member.

34. The method of claim 24, wherein the fenestrations are unevenly distributed on surfaces of said first cylindrical fenestrated member and said second cylindrical fenestrated member.

35. The method of claim 34, wherein the fenestrations are distributed on 5-50% of the surfaces of said first cylindrical fenestrated member and said second cylindrical fenestrated member.

36. The method of claim 24, wherein the fenestrations of said first cylindrical fenestrated member and said second cylindrical fenestrated member are of variable porosity.

37. The method of claim 24, wherein the fenestrations of said first cylindrical fenestrated member and said second cylindrical fenestrated member widen passing through each fenestration.

38. The method of claim 24, wherein said first and said second cylindrical fenestrated members have opposed distal and proximal ends and the fenestrations on said first cylindrical fenestrated member and said second cylindrical fenestrated member extend along one or more linear paths between said distal and said proximal ends of said first and said second cylindrical fenestrated members.

39. The method of claim 24, wherein at least one of said fenestrations further comprises a filter.

40. The method of claim 24, wherein said outer housing, said first cylindrical fenestrated member, said second cylindrical fenestrated member, and said rod are made from plastics, polymers, rubber materials, metals, alloys, glass, quartz, ceramics, or mixtures thereof.

41. The method of claim 24, wherein there are either: (a) four stop units, thereby allowing about a 90 degree rotation of said rod and said plunger; (b) three stop units, thereby allowing about a 120 degree rotation of said rod and said plunger; (c) two stop units, thereby allowing about a 180 degree rotation of said rod and said plunger; or (d) one stop unit, thereby allowing about a 360 degree rotation of said rod and said plunger.

42. The method of claim 24, wherein said elongate rod has 1, 2, 3, or 4 ribs.

43. The method of claim 24, wherein the plurality of longitudinally-extending ribs extend varying radial distances relative to one another, whereby at least one rib does not engage said stop units.

44. The method of claim 24, wherein the plurality of longitudinally-extending ribs extend to the same radial distances relative to one another, whereby all of the plurality of longitudinally-extending ribs engage said stop units.

45. The method of claim 24, wherein the ribs and said stop units are constructed so that the ribs rotate beyond said stop units in one rotational direction, but not in the opposite rotational direction.

46. The method of claim 24, wherein the ribs and said stop units are constructed so that said stop units matingly engage the ribs and hold said second cylindrical fenestrated member in the open or closed position.

47. The method of claim 24 further comprising:
a first end cap mounted on the ribs of said rod and engageable with inner surfaces of said outer housing near its proximal end, and
a second end cap to seal the inner tissue collection chamber at a location spaced from the inlet.

48. The method of claim 47, wherein said second cylindrical fenestrated member has a distal end surface which has an opening encompassing a portion of the end surface, said opening being at least partially covered when said second cylindrical fenestrated member is in the open position but not in the closed position.

49. The method of claim 24, wherein the system further comprises:
a valve proximate to the inlet to open and close the inlet.

50. The method of claim 24, wherein the system further comprises:
an inlet cap to seal and cover the inlet.

\* \* \* \* \*